United States Patent
Powell

(10) Patent No.: US 11,648,047 B2
(45) Date of Patent: May 16, 2023

(54) SYSTEM AND METHOD TO TREAT OBSTRUCTIVE SLEEP APNEA

(71) Applicant: Charles Lee Powell, Irving, TX (US)

(72) Inventor: Charles Lee Powell, Irving, TX (US)

(73) Assignee: VIVE SCIENTIFIC, LLC, Irving, TX (US)

( * ) Notice: Subject to any disclaimer, the term of this patent is extended or adjusted under 35 U.S.C. 154(b) by 1139 days.

(21) Appl. No.: 16/155,213

(22) Filed: Oct. 9, 2018

(65) Prior Publication Data

US 2019/0105098 A1 Apr. 11, 2019

Related U.S. Application Data

(60) Provisional application No. 62/568,848, filed on Oct. 6, 2017.

(51) Int. Cl.

| | | |
|---|---|---|
| *A61B 18/14* | (2006.01) | |
| *A61B 5/08* | (2006.01) | |
| A61B 18/12 | (2006.01) | |
| A61B 18/00 | (2006.01) | |
| A61B 5/01 | (2006.01) | |
| A61B 5/00 | (2006.01) | |
| A61B 90/00 | (2016.01) | |

(52) U.S. Cl.
CPC .......... *A61B 18/14* (2013.01); *A61B 18/1485* (2013.01); *A61B 5/01* (2013.01); *A61B 5/0826* (2013.01); *A61B 5/4552* (2013.01); *A61B 5/4818* (2013.01); *A61B 18/1206* (2013.01); *A61B 2018/00327* (2013.01); *A61B 2018/00702* (2013.01); *A61B 2018/00726* (2013.01); *A61B 2018/00761* (2013.01); *A61B 2018/00791* (2013.01); *A61B 2018/00797* (2013.01); *A61B 2090/036* (2016.02)

(58) Field of Classification Search
CPC .... A61B 18/1206; A61B 18/14; A61B 5/4818
See application file for complete search history.

(56) References Cited

U.S. PATENT DOCUMENTS

| | | |
|---|---|---|
| 3,897,787 A | 8/1975 | Ikuno |
| 3,971,383 A | 7/1976 | Van Gerven |
| 3,980,085 A | 9/1976 | Ikuno |

(Continued)

OTHER PUBLICATIONS

International Search Report and Written Opinion regarding PCT/US2018/054991, dated Dec. 21, 2018.

*Primary Examiner* — Michael F Peffley
*Assistant Examiner* — Samantha M Good
(74) *Attorney, Agent, or Firm* — Polsinelli PC

(57) ABSTRACT

A system is provided to treat sleep apnea, with a method of use. The system includes a handpiece which includes at least one penetrating electrode configured to penetrate tissue and one or more temperature sensors. A processor is coupled with the one or more temperature sensors and the at least one penetrating electrode, and a memory is configured to store instructions executable by the processor. The instructions, when executed, are operable to emit, by the at least one penetrating electrode, RF energy from the electrodes to heat a region of a base of a tongue until a target energy is delivered to the region. The instructions are also operable to measure, by the one or more temperature sensors, the temperature of the region.

11 Claims, 4 Drawing Sheets

(56) References Cited

U.S. PATENT DOCUMENTS

| | | |
|---|---|---|
| 4,171,700 A | 10/1979 | Farin |
| 4,244,371 A | 1/1981 | Farin |
| 4,278,090 A | 7/1981 | Van Gerven |
| 4,338,940 A | 7/1982 | Ikuno |
| 4,569,345 A | 2/1986 | Manes |
| 4,574,801 A | 3/1986 | Manes |
| 4,658,815 A | 4/1987 | Farin |
| 4,716,897 A | 1/1988 | Noguchi |
| 4,765,331 A | 8/1988 | Petruzzi |
| 4,823,791 A | 4/1989 | D'Amelio |
| 4,860,745 A | 8/1989 | Farin |
| 4,936,842 A | 6/1990 | D'Amelio |
| 5,122,137 A | 6/1992 | Lennox |
| 5,167,658 A | 12/1992 | Ensslin |
| 5,197,962 A | 3/1993 | Sansom |
| 5,226,904 A | 7/1993 | Gentelia |
| 5,281,216 A | 1/1994 | Klicek |
| 5,304,763 A | 4/1994 | Ellman |
| 5,342,359 A | 8/1994 | Rydell |
| 5,401,274 A | 3/1995 | Kusunoki |
| 5,438,302 A | 8/1995 | Goble |
| 5,496,312 A | 3/1996 | Klicek |
| 5,531,743 A | 7/1996 | Nettekoven |
| 5,540,684 A | 7/1996 | Hassler |
| 5,573,424 A | 11/1996 | Poppe |
| 5,626,575 A | 5/1997 | Crenner |
| 5,685,878 A | 11/1997 | Falwell |
| 5,702,387 A | 12/1997 | Arts |
| 5,718,702 A | 2/1998 | Edwards |
| 5,733,282 A | 3/1998 | Ellman |
| 5,792,139 A | 8/1998 | Chambers |
| 5,843,080 A | 12/1998 | Fleenor |
| 5,846,237 A | 12/1998 | Nettekoven |
| 5,919,191 A | 7/1999 | Lennox |
| 5,944,715 A | 8/1999 | Goble |
| 5,954,717 A | 9/1999 | Behl |
| 6,015,406 A | 1/2000 | Goble |
| 6,039,735 A | 3/2000 | Greep |
| 6,070,444 A | 6/2000 | Lontine |
| 6,080,149 A | 6/2000 | Huang |
| 6,090,106 A | 7/2000 | Goble |
| 6,109,268 A | 8/2000 | Thapliyal |
| 6,126,657 A * | 10/2000 | Edwards ............ A61B 18/1485 606/45 |
| 6,139,547 A | 10/2000 | Lontine |
| 6,152,921 A | 11/2000 | Gminder |
| 6,149,620 A | 12/2000 | Baker |
| 6,174,308 B1 | 1/2001 | Goble |
| 6,203,541 B1 | 3/2001 | Keppel |
| 6,214,003 B1 | 4/2001 | Morgan |
| 6,216,704 B1 | 4/2001 | Ingle |
| 6,267,760 B1 | 7/2001 | Swanson |
| 6,277,115 B1 | 8/2001 | Saadat |
| 6,296,636 B1 | 10/2001 | Cheng |
| 6,306,129 B1 | 10/2001 | Little |
| 6,312,408 B1 | 11/2001 | Eggers |
| 6,328,735 B1 | 12/2001 | Curley |
| 6,336,926 B1 | 1/2002 | Goble |
| 6,355,032 B1 | 3/2002 | Hovda |
| 6,355,033 B1 | 3/2002 | Moorman |
| 6,391,005 B1 | 5/2002 | Lum |
| 6,413,255 B1 | 7/2002 | Stern |
| 6,425,912 B1 | 7/2002 | Knowlton |
| 6,445,957 B1 | 9/2002 | Bolmsjo |
| 6,451,016 B1 | 9/2002 | Karakozian |
| 6,458,124 B1 | 10/2002 | Garito |
| 6,470,219 B1 | 10/2002 | Edwards |
| 6,565,560 B1 | 5/2003 | Goble |
| 6,565,561 B1 | 5/2003 | Goble |
| 6,620,156 B1 | 9/2003 | Garito |
| 6,632,193 B1 | 10/2003 | Davison |
| 6,682,501 B1 | 1/2004 | Nelson |
| 6,689,130 B2 | 2/2004 | Arai |
| 6,699,237 B2 | 3/2004 | Weber |
| 6,706,038 B2 | 3/2004 | Francischelli |
| 6,751,507 B2 | 6/2004 | Morrison |
| 6,758,846 B2 | 7/2004 | Goble |
| 6,763,836 B2 | 7/2004 | Tasto |
| 6,780,177 B2 | 8/2004 | Shafirstein |
| 6,837,884 B2 | 1/2005 | Woloszko |
| 6,843,789 B2 | 1/2005 | Goble |
| 6,893,435 B2 | 5/2005 | Goble |
| 6,905,480 B2 | 6/2005 | Mcguckin |
| 6,905,496 B1 | 6/2005 | Ellman |
| 6,911,027 B1 | 6/2005 | Edwards |
| 6,929,642 B2 | 8/2005 | Xiao |
| 6,939,350 B2 | 9/2005 | Phan |
| 6,949,096 B2 | 9/2005 | Davison et al. |
| 6,951,559 B1 | 10/2005 | Greep |
| 6,955,674 B2 | 10/2005 | Eick |
| 6,984,231 B2 | 1/2006 | Goble |
| 6,989,010 B2 | 1/2006 | Francischelli |
| 7,001,379 B2 | 2/2006 | Behl |
| 7,022,121 B2 | 4/2006 | Stern |
| 7,070,597 B2 | 7/2006 | Truckai |
| 7,125,409 B2 | 10/2006 | Truckai |
| 7,160,291 B2 | 1/2007 | Damasco |
| 7,172,589 B2 | 2/2007 | Lafontaine |
| 7,226,447 B2 | 6/2007 | Uchida |
| 7,232,438 B2 | 6/2007 | Long |
| 7,250,047 B2 | 7/2007 | Anderson |
| 7,282,047 B2 | 10/2007 | Zimmerman |
| 7,303,557 B2 | 12/2007 | Wham |
| 7,344,534 B2 | 3/2008 | Long |
| 7,377,918 B2 | 5/2008 | Amoah |
| 7,393,350 B2 | 7/2008 | Maurice |
| 7,393,351 B2 | 7/2008 | Woloszko |
| 7,407,503 B2 | 8/2008 | Difrancesco |
| 7,445,618 B2 | 11/2008 | Eggers |
| 7,458,972 B2 | 12/2008 | Keppel |
| 7,479,140 B2 | 1/2009 | Ellman |
| 7,481,807 B2 | 1/2009 | Knudsen |
| 7,520,877 B2 | 4/2009 | Lee |
| 7,556,627 B2 | 7/2009 | Long |
| 7,601,150 B2 | 10/2009 | Farin |
| 7,637,906 B2 | 12/2009 | Koop |
| 7,637,907 B2 | 12/2009 | Blaha |
| 7,691,097 B2 | 4/2010 | Miyazawa |
| 7,691,101 B2 | 4/2010 | Davison |
| 7,722,605 B2 | 5/2010 | Kawabata |
| 7,736,357 B2 | 6/2010 | Lee |
| 7,736,359 B2 | 6/2010 | Mcpherson |
| 7,744,596 B2 | 6/2010 | Young |
| 7,769,469 B2 | 8/2010 | Carr |
| 7,780,657 B2 | 8/2010 | Abboud |
| 7,789,883 B2 | 9/2010 | Takashino |
| 7,799,020 B2 | 9/2010 | Shores |
| 7,803,152 B2 | 9/2010 | Honda |
| 7,815,634 B2 | 10/2010 | Mcclurken |
| 7,819,864 B2 | 10/2010 | Morgan |
| 7,824,399 B2 | 11/2010 | Francischelli |
| 7,837,685 B2 | 11/2010 | Weinberg |
| 7,867,229 B2 | 1/2011 | Hayashida |
| 7,922,714 B2 | 4/2011 | Stevens-Wright |
| 7,942,869 B2 | 5/2011 | Houbolt |
| 7,955,330 B2 | 6/2011 | Platt |
| 7,959,628 B2 | 6/2011 | Schaer |
| 7,959,633 B2 | 6/2011 | Sartor |
| 7,972,329 B2 | 7/2011 | Refior |
| 8,034,050 B2 | 10/2011 | Sharareh |
| 8,034,052 B2 | 10/2011 | Podhajsky |
| 8,066,697 B2 | 11/2011 | Zvuloni |
| 8,092,449 B2 | 1/2012 | Desinger |
| 8,092,450 B2 | 1/2012 | Davies |
| 8,096,988 B2 | 1/2012 | Jarrard |
| 8,100,895 B2 | 1/2012 | Panos |
| 8,103,355 B2 | 1/2012 | Mulholland |
| 8,105,323 B2 | 1/2012 | Buysse |
| 8,109,927 B2 | 2/2012 | Kelly |
| 8,109,929 B2 | 2/2012 | Eitenmueller |
| 8,114,072 B2 | 2/2012 | Long |
| 8,150,532 B2 | 4/2012 | Karni |
| 8,152,799 B2 | 4/2012 | Ormsby |
| 8,157,795 B2 | 4/2012 | Sartor |

(56) References Cited

U.S. PATENT DOCUMENTS

| | | |
|---|---|---|
| 8,157,796 B2 | 4/2012 | Collins |
| 8,187,263 B2 | 5/2012 | Behnke |
| 8,192,427 B2 | 6/2012 | Buysse |
| 8,202,271 B2 | 6/2012 | Orszulak |
| 8,211,103 B2 | 7/2012 | Greep |
| 8,216,219 B2 | 7/2012 | Desinger |
| 8,216,224 B2 | 7/2012 | Morris |
| 8,216,229 B2 | 7/2012 | Elliott |
| 8,216,234 B2 | 7/2012 | Long |
| 8,216,235 B2 | 7/2012 | Rioux |
| 8,231,622 B2 | 7/2012 | Bacher |
| 8,246,616 B2 | 8/2012 | Amoah |
| 8,251,995 B2 | 8/2012 | Platt |
| 8,287,526 B2 | 10/2012 | Arless |
| 8,287,533 B2 | 10/2012 | Wittkampf |
| 8,292,887 B2 | 10/2012 | Woloszko |
| 8,303,580 B2 | 11/2012 | Wham |
| 8,313,482 B2 | 11/2012 | Mcintyre |
| 8,337,494 B2 | 12/2012 | Suslov |
| 8,348,940 B2 | 1/2013 | Behl |
| 8,357,151 B2 | 1/2013 | Goldberg |
| 8,361,068 B2 | 1/2013 | Mcclurken |
| 8,382,753 B2 | 2/2013 | Truckai |
| 8,388,612 B2 | 3/2013 | Dunning |
| 8,398,626 B2 | 3/2013 | Buysse |
| 8,430,873 B2 | 4/2013 | Gregg |
| 8,449,536 B2 | 5/2013 | Selig |
| 8,449,539 B2 | 5/2013 | Wang |
| 8,465,483 B2 | 6/2013 | Lario |
| 8,469,954 B2 | 6/2013 | Young |
| 8,475,447 B2 | 7/2013 | Orszulak |
| 8,486,061 B2 | 7/2013 | Podhajsky |
| 8,500,727 B2 | 8/2013 | Aramayo |
| 8,523,849 B2 | 9/2013 | Liu |
| 8,523,855 B2 | 9/2013 | Keppel |
| 8,523,856 B2 | 9/2013 | Sampson |
| 8,540,705 B2 | 9/2013 | Mehta |
| 8,545,490 B2 | 10/2013 | Mihajlovic |
| 8,556,892 B2 | 10/2013 | Hong |
| 8,568,407 B2 | 10/2013 | Brannan |
| 8,568,409 B2 | 10/2013 | O'Brien |
| 8,628,524 B2 | 1/2014 | Shilev |
| 8,628,527 B2 | 1/2014 | Brannan |
| 8,632,529 B2 | 1/2014 | Bencini |
| 8,758,337 B2 | 1/2014 | Skwarek |
| 8,647,340 B2 | 2/2014 | Blaha |
| 8,652,130 B2 | 2/2014 | Kreindel |
| 8,663,223 B2 | 3/2014 | Masuda |
| 8,679,111 B2 | 3/2014 | Oyola |
| 8,679,112 B2 | 3/2014 | Geitz |
| 8,690,867 B2 | 4/2014 | Dunning |
| 8,728,071 B2 | 5/2014 | Lischinsky |
| 8,728,072 B2 | 5/2014 | Eder |
| 8,795,270 B2 | 8/2014 | Drake |
| 8,795,272 B2 | 8/2014 | Rioux |
| 8,795,273 B2 | 8/2014 | Yanuma |
| 8,814,856 B2 | 8/2014 | Elmouelhi |
| 8,840,610 B2 | 9/2014 | Humble |
| 8,845,630 B2 | 9/2014 | Mehta |
| 8,870,861 B2 | 10/2014 | El-Galley |
| 8,882,758 B2 | 11/2014 | Nebrigic |
| 8,888,768 B2 | 11/2014 | Babkin |
| 8,906,051 B2 | 12/2014 | Mitelberg |
| 8,920,412 B2 | 12/2014 | Fritz |
| 8,920,415 B2 | 12/2014 | Govari |
| 8,939,968 B2 | 1/2015 | Geiselhart |
| 8,945,109 B2 | 2/2015 | Mehta |
| 8,945,124 B2 | 2/2015 | Craig |
| 8,956,347 B2 | 2/2015 | Lorang |
| 8,968,295 B2 | 3/2015 | Orszulak |
| 8,968,298 B2 | 3/2015 | Twomey |
| 8,974,455 B2 | 3/2015 | Bacher |
| 8,979,836 B2 | 3/2015 | Fischer |
| 8,986,300 B2 | 3/2015 | Govari |
| 8,998,895 B2 | 4/2015 | Besch |
| 9,005,192 B2 | 4/2015 | Govari |
| 9,005,193 B2 | 4/2015 | Govari |
| 9,011,419 B2 | 4/2015 | Flyash |
| 9,011,424 B2 | 4/2015 | Werner |
| 9,023,028 B2 | 5/2015 | Bystryak |
| 9,050,081 B2 | 6/2015 | Fischer |
| 9,050,089 B2 | 6/2015 | Orszulak |
| 9,055,959 B2 | 6/2015 | Vaska |
| 9,060,774 B2 | 6/2015 | Eisele |
| 9,066,738 B2 | 6/2015 | Mehta |
| 9,072,525 B2 | 7/2015 | Shin |
| 9,078,663 B2 | 7/2015 | Geiselhart |
| 9,084,590 B2 | 7/2015 | Wittenberger |
| 9,113,888 B2 | 8/2015 | Orszulak |
| 9,113,896 B2 | 8/2015 | Mulier |
| 9,119,623 B2 | 9/2015 | Malis |
| 9,119,624 B2 | 9/2015 | Wham |
| 9,149,322 B2 | 10/2015 | Knowlton |
| 9,155,583 B2 | 10/2015 | Bek |
| 9,155,590 B2 | 10/2015 | Mathur |
| 9,192,423 B2 | 11/2015 | Schall |
| 9,192,440 B2 | 11/2015 | Rossetto |
| 9,198,705 B2 | 12/2015 | Qin |
| 9,198,720 B2 | 12/2015 | Heard |
| 9,265,563 B2 | 2/2016 | Racz |
| 9,271,790 B2 | 3/2016 | Collins |
| 9,283,032 B2 | 3/2016 | Thomas |
| 9,283,035 B2 | 3/2016 | Lanphere |
| 9,289,254 B2 | 3/2016 | Selig |
| 9,308,039 B2 | 4/2016 | Azure |
| 9,314,302 B2 | 4/2016 | Dougal |
| 9,314,620 B2 | 4/2016 | Long |
| 9,326,810 B2 | 5/2016 | Shilev |
| 9,339,326 B2 | 5/2016 | Mccullagh |
| 9,345,541 B2 | 5/2016 | Greeley |
| 9,351,785 B2 | 5/2016 | Hong |
| 9,351,787 B2 | 5/2016 | Edwards |
| 9,375,244 B2 | 6/2016 | Orszulak |
| 9,375,246 B2 | 6/2016 | Podhajsky |
| 9,375,252 B2 | 6/2016 | Coe |
| 9,381,061 B2 | 7/2016 | Mcclurken |
| 9,456,873 B2 | 10/2016 | Beardsley |
| 9,463,063 B2 | 10/2016 | Seddon |
| 9,486,283 B2 | 11/2016 | Greeley |
| 9,532,828 B2 | 1/2017 | Condie |
| 9,539,052 B2 | 1/2017 | Edwards |
| 9,566,113 B2 | 2/2017 | Werneth |
| 9,572,623 B2 | 2/2017 | Long |
| 9,585,711 B2 | 3/2017 | Marion |
| 9,597,151 B2 | 3/2017 | Brannan |
| 9,707,027 B2 | 7/2017 | Ruddenklau |
| 9,730,751 B2 | 8/2017 | Van Wyk |
| 9,743,975 B2 | 8/2017 | Brannan |
| 9,839,466 B2 | 12/2017 | Utley |
| 2001/0014806 A1 | 8/2001 | Ellman |
| 2002/0052601 A1 | 5/2002 | Goldberg |
| 2002/0115917 A1 | 8/2002 | Honda |
| 2003/0109865 A1 | 6/2003 | Greep |
| 2003/0130652 A1 | 7/2003 | Wittenberger |
| 2003/0139789 A1 | 7/2003 | Tvinnereim |
| 2004/0181219 A1 | 9/2004 | Goble |
| 2005/0107779 A1 | 5/2005 | Ellman |
| 2005/0113818 A1 | 5/2005 | Sartor |
| 2005/0187599 A1 | 8/2005 | Sharkey |
| 2005/0222562 A1 | 10/2005 | Lovewell |
| 2006/0095031 A1 | 5/2006 | Ormsby |
| 2007/0100331 A1 | 5/2007 | Young |
| 2007/0179491 A1 | 8/2007 | Kratoska |
| 2008/0051776 A1 | 2/2008 | Bliweis |
| 2008/0077128 A1 | 3/2008 | Woloszko |
| 2008/0119846 A1 | 5/2008 | Rioux |
| 2008/0200969 A1 | 8/2008 | Weber |
| 2008/0215046 A1 | 9/2008 | Messing |
| 2008/0287948 A1 | 11/2008 | Newton |
| 2008/0312647 A1 | 12/2008 | Knopp |
| 2009/0043301 A1 | 2/2009 | Jarrard |
| 2009/0112205 A1 | 4/2009 | Mcgill |
| 2009/0209990 A1 | 8/2009 | Yates |
| 2009/0259221 A1 | 10/2009 | Tahara |

(56) References Cited

U.S. PATENT DOCUMENTS

| | | |
|---|---|---|
| 2010/0106157 A1 | 4/2010 | Umemoto |
| 2010/0198199 A1 | 8/2010 | Kreindel |
| 2010/0217254 A1 | 8/2010 | Mehta |
| 2010/0268221 A1 | 10/2010 | Beller |
| 2011/0060328 A1 | 3/2011 | Skwarek |
| 2011/0071516 A1 | 3/2011 | Gregg |
| 2011/0202048 A1 | 8/2011 | Nebrigic |
| 2011/0213365 A1 | 9/2011 | Eisele |
| 2011/0230878 A1 | 9/2011 | Ryan |
| 2011/0306969 A1 | 12/2011 | Coe |
| 2012/0022521 A1 | 1/2012 | Odom |
| 2012/0041431 A1 | 2/2012 | Levin |
| 2012/0123400 A1 | 5/2012 | Francischelli |
| 2012/0157992 A1 | 6/2012 | Smith |
| 2013/0018369 A1 | 1/2013 | Mihalik |
| 2013/0085495 A1 | 4/2013 | Young |
| 2013/0131671 A1 | 5/2013 | Baker |
| 2013/0253508 A1 | 9/2013 | Ide |
| 2013/0283607 A1 | 10/2013 | Zerfas |
| 2014/0005658 A1 | 1/2014 | Rosenbegr |
| 2014/0018791 A1 | 1/2014 | Hong |
| 2014/0046324 A1 | 2/2014 | Belson |
| 2014/0058378 A1 | 2/2014 | Brannan |
| 2014/0088588 A1 | 3/2014 | Jarrard |
| 2014/0107647 A1 | 4/2014 | Greeley |
| 2015/0032094 A1 | 1/2015 | Kane |
| 2015/0223865 A1 | 8/2015 | Krapohl |
| 2015/0230861 A1 | 8/2015 | Woloszko |
| 2015/0265334 A1 | 9/2015 | Franke |
| 2015/0359591 A1 | 12/2015 | Benisty |
| 2016/0287334 A1 | 10/2016 | Grant |
| 2016/0302842 A1 | 10/2016 | Barnes |
| 2016/0302858 A1 | 10/2016 | Bencini |
| 2016/0324566 A1 | 11/2016 | Kudo |
| 2016/0367307 A1 | 12/2016 | Ishikawa |
| 2016/0374744 A1 | 12/2016 | Akagane |
| 2017/0000541 A1 | 1/2017 | Yates |
| 2017/0000542 A1 | 1/2017 | Yates |
| 2017/0020592 A1 | 1/2017 | Utley |
| 2017/0035489 A1 | 2/2017 | Behnke |
| 2017/0049501 A1 | 2/2017 | Guirguis |
| 2017/0056099 A1 | 3/2017 | Hubelbank |
| 2017/0086903 A1 | 3/2017 | Sartor |
| 2017/0112562 A1 | 4/2017 | Woloszko |
| 2017/0143401 A1 | 5/2017 | Woloszko |
| 2017/0143402 A1 | 5/2017 | Fischer |
| 2017/0143419 A1 | 5/2017 | Ingle |
| 2017/0164996 A1 | 6/2017 | Honda |
| 2017/0172642 A1 | 6/2017 | Yuan |
| 2017/0189099 A1 | 7/2017 | Garrison |
| 2017/0215937 A1 | 8/2017 | Kudo |
| 2017/0215938 A1 | 8/2017 | Yasunaga |
| 2017/0224403 A1 | 8/2017 | Suzuki |
| 2017/0231682 A1 | 8/2017 | Avcioglu |
| 2017/0231685 A1 | 8/2017 | Weinberg |
| 2017/0245916 A1 | 8/2017 | Sugawara |
| 2017/0245921 A1 | 8/2017 | Joseph |
| 2017/0290618 A1 | 10/2017 | Lalonde |
| 2017/0296259 A1 | 10/2017 | Decarlo |
| 2017/0303988 A1 | 10/2017 | Hayashida |
| 2017/0319263 A1 | 11/2017 | Batchelor |
| 2017/0325869 A1 | 11/2017 | Brannan |
| 2017/0333108 A1 | 11/2017 | Nakamura |
| 2017/0333109 A1 | 11/2017 | Gilbert |
| 2017/0348049 A1* | 12/2017 | Vrba .................. A61B 18/1492 |
| 2017/0360496 A1 | 12/2017 | Faehsing |
| 2017/0367750 A1 | 12/2017 | Kudo |
| 2017/0367751 A1 | 12/2017 | Ruddenklau |

\* cited by examiner

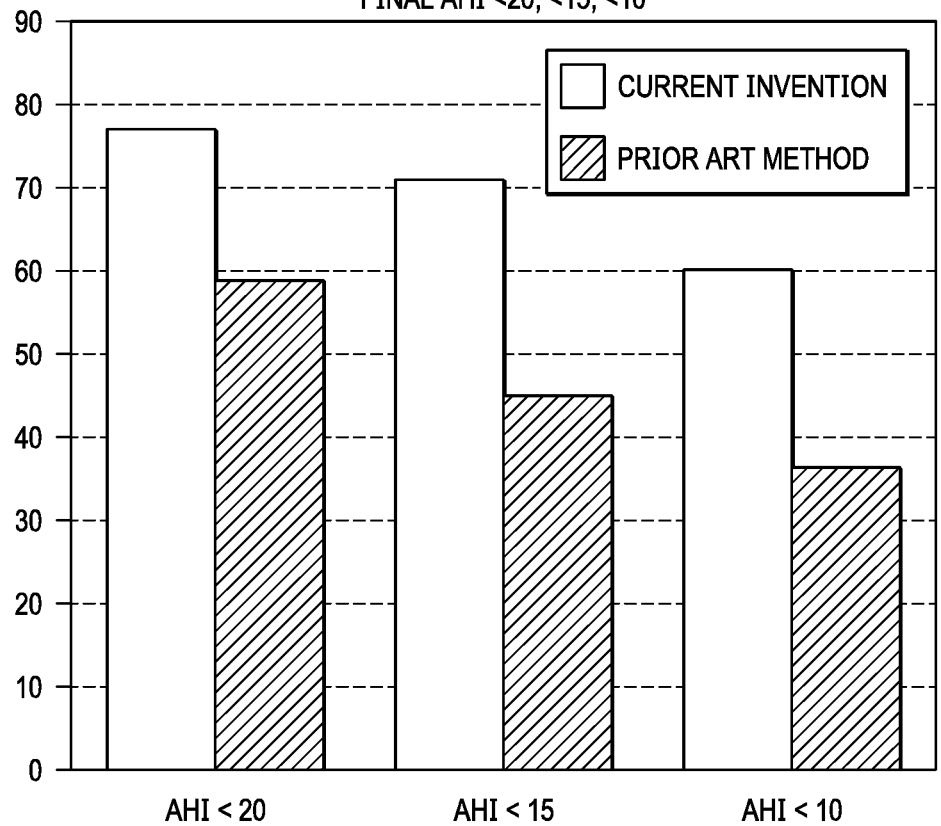

SYSTEM AND METHOD TO TREAT OBSTRUCTIVE SLEEP APNEA

CROSS-REFERENCE TO RELATED APPLICATION

This application claims benefit of U.S. Provisional Patent Application No. 62/568,848, which was filed in the U.S. Patent and Trademark Office on Oct. 6, 2017, all of which is incorporated herein by reference in its entirety for all purposes.

BACKGROUND

1. Field

The present disclosure relates generally to radiofrequency ablation. In particular, the present disclosure relates to soft palate and tongue base treatment devices and methods operable to treat obstructive sleep apnea via radiofrequency tightening of tissue.

2. Discussion of Related Art

Obstructive sleep apnea (OSA) can occur when soft tissue partially or completely blocks the upper airways during sleep. In OSA, breathing is repetitively stopped or slowed over the course of the night. In severe OSA, breathing can be stopped (apnea) or slowed (hypopnea) 30 or more times per hour. With each occurrence, elevated blood $CO_2$ levels cause the person to wake up, significantly impacting quality of sleep. OSA can be associated with obesity, although 28% of OSA sufferers have a normal body mass index. Fatigue often leads to increased intake of starchy and fatty foods, potentially worsening OSA.

90% of OSA associated obstructions are caused by the base of the tongue and/or soft palate, while other sources of OSA only account for 10% of obstructions.

Obstructive sleep apnea can cause fatigue, dry mouth, headaches, depression, decreased ability to concentrate, memory loss, and irregular heart rhythms. Over a longer term, OSA can be associated with increased risk of stroke, cardiovascular disease, dementia, hypertension, and type II diabetes. Long term effects of OSA can even result in death. It is estimated that OSA can decrease a lifespan by 8-20 years. OSA is thought to result in as much as a seven-fold increase in risk of automobile accidents, resulting in 6,000-10,000 death annually in the United States—15-20% of total automobile accident related deaths.

Often, OSA can be diagnosed and severity quantified based on the "Apnea Hypopnea Index" or AHI, which is the number of apnea or hypopnea events per hour. In order for an event to be classified as hypopnea and counted in the AHI, there must be a >30% reduction in airflow of greater than 10 seconds in duration, associated with arousal, and/or a threshold reduction in blood oxygenation. The American Academy of Sleep Medicine recommends that an oxygen desaturation of 3% be used as a threshold to identify hypopnea, although the use of 4% is also acceptable. An AHI less than 5 is considered to be normal, AHI of 5 or greater but less than 15 is considered mild OSA, an AHI of 15 or greater but less than 30 is considered moderate OSA, and an AHI of 30 or greater is considered to be severe OSA.

OSA can be diagnosed via a sleep study, such as an in-clinic polysomnogram (PSG) or a home sleep study (HST). PSG has the advantages of collecting much more data in a controlled environment. However, HST has the advantage of being conducted in the subjects' actual sleep environment. Sleep studies include measurements of the number of apnea and hypopnea events per hour (AHI), the respiratory distress index (RDI) which in addition to the events measured by the AHI includes less severe respiratory related sleep disturbances, the percent of time spent with an oxygen saturation below 90%, the percent time and loudness of snoring, and the mean pulse rate. Also measured are the duration of sleep, the time to fall asleep ("sleep latency"), and the percentage of time spent asleep ("sleep efficiency"). It is believed that 24% of men in the United States have at least mild sleep apnea, as defined as an AHI of 5 or more. 4% of women and 9% of men in the United States suffer from moderate (AHI≥15) or severe (AHI≥30) OSA.

Upon diagnosis of OSA, a patient is usually first offered the use of a continuous positive airway pressure (CPAP) device, in conjunction with behavior modification such as weight loss, change in sleep positions, and/or avoidance of alcohol and soporific drugs (sleeping pills). CPAP, introduced in 1981, utilizes a face mask and an air compressor to generate elevated pressure in the airways, essentially inflating the airways to keep them open. Although CPAP generally succeeds in keeping airways open, it requires the subject to wear a facemask connected by a hose to a somewhat noisy air compressor, which many patients find uncomfortable and distracting. As such, many patients feel that they have substituted one sleeping disorder for another.

Oral appliances can be worn during sleeping to pull the jaw forward and open the airway. The oral appliances can be less efficacious than CPAP. Like CPAP, the oral appliances can be uncomfortable to wear and suffer from similar non-compliance to CPAP. They can also cause long term issues due to the displacement of the jaw.

Surgery focused on enlarging and stabilizing the airway, such as Uvulopalatopharyngoplasty, can be performed in an operating room under general anesthesia. However, recovery may be up to two weeks and side effects can include throat discomfort, bleeding, swallowing problems, and anesthesia complications.

Minimally invasive techniques utilizing lasers can also be utilized as a treatment for OSA. For example, Fotona Nightlase utilizes a laser to modify the soft palate. Systems can also utilize radiofrequency (RF) ablation to heat tissue, forming scar tissue that is absorbed, which firms up and minimizes the amount of tissue (for example in the base of the tongue or soft palate) available to block the airway.

As such, it is desirable to provide a system which can enable a minimally invasive procedure to treat sleep apnea which does not require the use of uncomfortable facemasks, noisy compressors, or uncomfortable oral appliances during sleeping. Additionally, it is desirable to provide a device and method for directed delivery of RF power that has improved efficacy in the treatment of obstructive sleep apnea than existing RF technologies.

SUMMARY

The present inventive concept provides a system and method for a minimally invasive procedure to treat sleep apnea which does not require the use of uncomfortable facemasks, noisy compressors, or uncomfortable oral appliances during sleeping. Additionally, the present inventive concept provides a device and method for directed delivery of RF power that has improved efficacy in the treatment of obstructive sleep apnea than existing RF technologies.

The present inventive concept delivers RF power to the base of the tongue and/or the soft palate. To treat the base of the tongue, two RF ablation cycles are performed with a cooling cycle in between the two RF ablation cycles. During each RF ablation cycle, RF energy is delivered to the base of the tongue until a target energy is delivered to the treated region. The RF energy can be delivered by at least one electrode, for example penetrating electrodes which penetrate the tissue of the treated region. The target energy for each RF ablation cycle can be the same. In other examples, the target energy for each RF ablation cycle can be different. Additionally, during each RF ablation cycle, the temperature of the treated region is measured by temperature sensors. The temperature of the region does not exceed a target temperature. The target temperature for each RF ablation cycle can be the same. In other examples, the target temperature for each RF ablation cycle can be different.

To treat the soft palate, RF energy is delivered to a region of the soft palate until a target temperature is reached. After the target temperature is reached, RF energy is delivered such that the target temperature is maintained for a predetermined period of time. To treat the soft palate, the RF energy can be delivered by at least one electrode, for example surface electrodes which are pressed against the treated region. After the region is treated, the electrodes can be moved to another region of the soft palate and treated. The process can be repeated in multiple regions until the desired regions of the soft palate are treated. For example, substantially the entire soft palate can be treated.

The system and method disclosed herein can control two or more deliveries of RF power to a target tissue without any intervention on the part of the user such as a physician, allowing the user to maintain focus on the patient and the location of the electrodes during the procedure.

These and other objects, advantages, and features will become apparent to those persons skilled in the art upon reading the details of the devices and methodologies as more fully described below.

BRIEF DESCRIPTION OF THE DRAWINGS

Implementations of the present technology will now be described, by way of example only, with reference to the attached figures, wherein:

FIG. 6 is a chart comparing outcomes of the present inventive concept to a conventional procedure.

DETAILED DESCRIPTION

Figure 1:
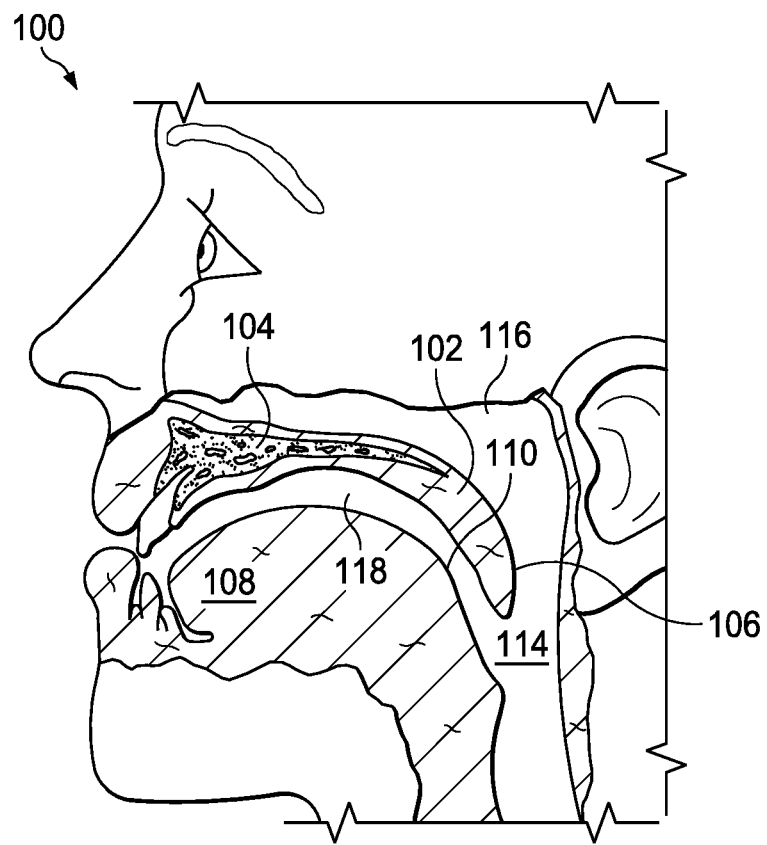
FIG. 1 is a diagram illustrating an exemplary environment for a device according to the present disclosure.

It will be appreciated that for simplicity and clarity of illustration, where appropriate, reference numerals have been repeated among the different figures to indicate corresponding or analogous elements. Individual features described herein can be utilized in any example and is not limited to the example with which the individual features are described. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to-scale and the proportions of certain parts may be exaggerated to better illustrate details and features of the present disclosure.

Before the present formulations and methods are described, it is to be understood that the disclosed subject matter is not limited to particular formulations and methods described, as such may vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present inventive concept. The upper and lower limits of these smaller ranges may independently be included or excluded in the range, and each range where either, neither, or both limits are included in the smaller ranges is also encompassed within the present inventive concept, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which the present inventive concept belongs. Although any methods and materials similar or equivalent to those described herein can be used in the practice or testing of the present subject matter, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present inventive concept is not entitled to antedate such publication by virtue of prior disclosure. Further, the dates of publication provided may be different from the actual publication dates which may need to be independently confirmed.

I. Definitions

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "outside" or "outer" refers to a region that is beyond the outermost confines of a physical object. The term "inside" or "inner" refers to a region that is within the outermost confines of a physical object. The term "substantially" is defined to be essentially conforming to the particular dimension, shape or other word that substantially modifies, such that the component need not be exact. For example, "substantially cylindrical" means that the object resembles a cylinder, but can have one or more deviations from a true cylinder. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees. The terms "comprising," "including" and "having" are used interchangeably in this disclosure. The terms "comprising," "including" and "having" mean to include, but not necessarily be limited to the things so described.

It must be noted that as used herein and in the appended claims, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

Radiofrequency, RF, and the like: A portion of the electromagnetic spectrum in the range 104 to 1012 Hz, used for example in telecommunications and radiofrequency ablation.

Radiofrequency Ablation, RF Ablation, RFA and the like: Radiofrequency ablation (or RFA) is a procedure used to reduce pain. An electrical current produced by a radio wave is used to heat up a small area of tissue such as at the base of the tongue or the soft palate, thereby firming up and/or minimizing the amount of tissue in that specific area.

Soft Palate and the like: A fleshy, flexible part toward the back of the roof of the mouth. The soft palate is distinguished from the hard palate which is toward the front of the mouth in that it does not contain bone. The soft palate comprises muscle fibers and is moveable. It is responsible for closing off the nasal passages and airway while swallowing and protecting the nasal passages during sneezing. The soft palate, along with the back of the tongue, can be responsible for many airway obstructions in obstructive sleep apnea.

Obstructive Sleep Apnea, Sleep Apnea, OSA, and the like: A condition wherein soft tissue partially or completely blocks the upper airways during sleep. As such, breathing is repetitively stopped or slowed over the course of the night.

Apnea, Apnoea, and the like: The cessation of or pause in breathing for a predetermined amount of time.

Hypopnea, Hypopnoea, and the like: Overly shallow breathing or an abnormally low respiratory rate.

Apnea Hypopnea Index, AHI, and the like: An index used to quantify the severity of sleep apnea. It is represented by the number of apnea and hypopnea events per hour of sleep. To be included in the AHI, apnea events must last for at least 10 seconds, and Hypopnea must comprise a >30% reduction in airflow of greater than 10 seconds in duration, associated with arousal, and/or a threshold reduction in blood oxygenation. The AHI is calculated by dividing the number of apnea and hypopnea events by the number of hours of sleep. The AHI values for adults are categorized as:
  Normal: AHI<5;
  Mild sleep apnea: 5≤AHI<15;
  Moderate sleep apnea: 15≤AHI<30;
  Severe sleep apnea: AHI≥30.

Body Mass Index, BMI, and the like: An index used to assess body fat and obesity. BMI is calculated as a person's weight in kilograms divided by their height in meters.

Polysomnography: a sleep study conducted at a clinical site where brain waves, eye movements, heart rate, breathing pattern, blood oxygen level, body position, limb movement, and snoring are monitored and recorded.

Polysomnogram, PSG, and the like: a continuous graph of the sleep parameters measured in polysomnography.

Sleep study: a study wherein breathing and other parameters are monitored, preferably for the diagnosis of obstructive sleep apnea. Sleep studies can be home sleep studies, or polysomnography conducted in clinic.

Home Sleep Study, HST, and the like: A sleep study conducted in the home. HST in general does not measure all the parameters monitored in polysomnography, but has the advantage of being simpler, less expensive, and occurring in the natural sleep setting.

Respiratory Distress Index, RDI, and the like: An index used in the diagnosis of obstructive sleep apnea which, in addition to the events measured by the apnea hypopnea index, includes less severe respiratory related sleep disturbances called Respiratory-Effort Related Arousals, (RERAs)

Respiratory-Effort Related Arousal, RERA, and the like: Arousals from sleep measured during polysomnography that do not technically meet the definitions of apneas or hypopneas but do disrupt sleep. They are abrupt transitions from a deeper stage of sleep to a shallower.

Sleep Latency: The time it takes to fall asleep, for example during a sleep study.

Sleep Efficiency: The time spent asleep, as a percentage of the time spent in bed, for example during a sleep study.

Hypopnea Desaturation Criterion: A criterion used in the inclusion of a hypopnea event in an index such as the Apnea Hypopnea Index or the respiratory distress index. Preferably a hypopnea desaturation criterion of ≥3% oxygen desaturation from pre-event baseline is used. However, it is acceptable to score hypopneas when there is a ≥4% oxygen desaturation from pre-event baseline.

Soporific Drugs, Soporifics, Sleeping Pills, and the like: a class of psychoactive drugs whose primary function is to induce sleep for use in insomnia or surgical anesthesia Continuous Positive Airway Pressure, CPAP, and the like: A system for treating obstructive sleep apnea wherein a face mask and air compressor are used to induce pressure above ambient in the airways, keeping them inflated and reducing obstruction. While CPAP is in general efficacious in removing airway obstruction, the system can be uncomfortable to wear and noisy, resulting in low compliance and often causing sleeplessness.

Uvulopalatopharyngoplasty, UPPP, UP3, and the like: A surgical procedure used to treat obstructive sleep apnea via the removal tissue and/or the remodeling of tissue in the airway.

Somnolence, sleepiness, drowsiness, and the like: A state of strong desire for sleep, or sleeping for unusually long periods Lowest Oxygen Saturation, LSAT, and the like: The lowest oxygen saturation measured, for example, during a sleep study. Lowest oxygen saturation can be used as a measure of severity of obstructive sleep apnea. The change in lowest oxygen saturation from baseline can be used as a measure of the efficacy of a treatment.

Standard Error of the Mean, SEM, and the like: The standard deviation of a series of measurements divided by the square root of the number of measurements. Unlike the standard deviation, the standard error of the mean reflects how a larger number of measurements provides a better estimate of the actual underlying value of a parameter relative to a smaller number of measurements.

Tumescence: The quality or state of being swollen, for example due to the injection of a tumescence fluid. Tumescence can improve the efficacy of radio frequency ablation of the back of the tongue.

Tumescence Fluid: A fluid that is injected to cause tumescence. For example, tumescence fluid can be injected in the back of the tongue to cause tumescence immediately prior to radio frequency ablation treatment for obstructive sleep apnea.

Radio Frequency Tissue Tightening Cycle, RF Tissue Tightening Cycle, and the like: A portion of the treatment, for example to the soft palate, during which radio frequency power is applied. For example, the RF power heats the tissue to a target temperature and maintains the temperature for a predetermined amount of time. The tissue then tightens, for example shrinks to a smaller size.

Radio Frequency Ablation Cycle, RF Ablation Cycle, and the like: A portion of a radio frequency ablation treatment, for example to the back of the tongue, during which radio frequency power is applied. For example, a treatment can include two or more radio frequency ablation cycles, separated by one or more cooling cycles. A radio frequency ablation cycle can include a heating phase which can be followed by a maintenance phase.

Heating Phase: A portion of a radio frequency ablation cycle during which relatively high levels of radio frequency power can be applied, resulting in a local increase of temperature in the vicinity of the treatment. The amount of RF power applied may be the maximum that a system is capable of, or may be limited by a predetermined rate of temperature increase. The heating phase can be conducted until a pre-specified amount of energy is delivered, or until a predetermined temperature is reached, at which time the amount of radio frequency power is reduced such that the predetermined temperature is maintained in a maintenance phase.

Maintenance Phase: A portion of a radio frequency ablation cycle during which relatively low levels of radio frequency power are applied. The radio frequency power is selected to result in local maintenance of a predetermined temperature in the region of the treatment. The heating phase can be conducted for a predetermined time. For example, the heating phase can be conducted until a predetermined amount of energy is delivered during the maintenance phase. Also, the heating phase can be conducted until a pre-specified amount of energy is delivered during a combination of a heating phase and a maintenance phase.

Cooling Cycle: A portion of a radio frequency ablation treatment, for example to the back of the tongue, between two radio frequency ablation cycles, during which radio frequency power is not applied. A treatment can include two or more radio frequency ablation cycles, separated by one or more cooling cycles. A cooling cycle duration can be a predetermined amount of time, for example a cooling cycles can continue until a predetermined temperature is reached, whereupon the next radio frequency ablation cycle is started.

Penetrating Electrodes: Electrodes for delivering RF energy wherein the electrodes are sharpened and designed to penetrate the tissue being treated. Penetrating electrodes can include integrated temperature sensors and have stops for limiting the total amount of penetration. The tissue being treated with penetrating electrodes can be, for example, the back of the tongue.

Surface Electrodes: Electrodes for delivering RF energy wherein the contact surface of the electrodes is a two dimensional curved surfaces and is not designed to penetrate the tissue being treated, but rather to transmit RF power through surface contact. In at least one example, surface electrodes can include temperature sensors. For example, the tissue being treated with penetrating electrodes is the soft palate.

II. General Architecture

FIG. 1 illustrates mouth and airways 100. Mouth and airways 100 includes soft palate 102, uvula 106, tongue 108, and base of tongue 110, hard palate (showing bone) 104, mouth 118, nasal passage 116, and upper airway 114.

The muscles in soft palate 102 and uvula 106 are important in breathing, speaking, and swallowing. During swallowing, soft palate 102 closes off the nasal passages 116 and airway 114. In speech, "velar consonants" (such as the K sound) are produced by touching base of tongue 110 against soft palate 102. Soft palate 102 also closes off the nasal passage 116 during speech. Incomplete closure causes speech to sound "nasal".

In obstructive sleep apnea, airway 114 is partly or wholly blocked. The blockage may occur for a variety of reasons, for example base of tongue 110 or soft palate 102 blocking airway 114. Soft palate 102 may be enlarged or the tissues or muscles may have loosened. As such, when a person is sleeping, soft palate 102 may extend into airway 114 such that airway 114 is at least partly blocked.

Figure 2:
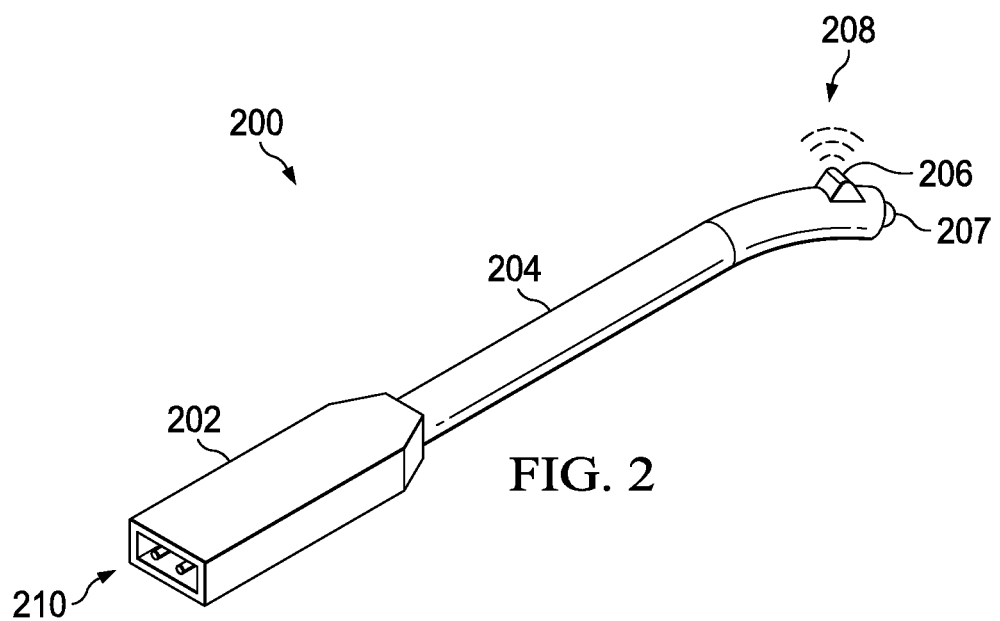
FIG. 2 is an illustration of an exemplary handpiece to treat a soft palate according to the present disclosure.

FIG. 2 illustrates an example of a handpiece 200 which can be utilized, for example, in the treatment for a soft palate. Handpiece 200 includes handle 202, extension 204, electrode 206, RF energy 208, and cord receptacle 210. The handle 202 is configured such that a user can hold the handle 202 and maneuver the handpiece 200. The handle 202 can be ergonomically configured. The handle 202 can have any suitable shape such that a user can hold the handle 202 with a hand. The extension 204 extends from the handle 202 for a predetermined length such that the electrode 206 can be positioned proximate to the soft palate 102. The extension 204 can be an extension of the handle 202. In at least one example, the cord receptacle 210 can connect the handpiece 200 to a workstation, for example workstation 400 described below. In some examples, the cord receptacle 210 can connect to a power source. In other examples, the handpiece 200 may not include a cord receptacle 210. Electrode 206 may be a penetrating electrode. As illustrated in FIG. 2, the electrode 206 can be a surface electrode. Soft palate handpiece 200 can include any suitable number of electrodes 206, for example 1, 2, 3, or more. FIG. 2 shows the soft palate handpiece 200 including one surface electrode 206. The electrode 206 is configured to emit RF energy 208 in a direction. As such, the user can position the electrode 206 to be proximate to the soft palate 102 such that the electrode 206 faces the soft palate 102 and emits RF energy 208 to the soft palate 102. The electrode 206 can emit a desired amount of RF energy 208 such that the soft palate 102 can be tightened. The electrode 206 can be coupled with a processor which can instruct the electrode 206 to emit the desired or predetermined amount of RF energy 208. After being exposed to the RF energy 208 for a predetermined amount of time, the soft palate 102 can be tightened to open the airway and prevent OSA.

Figure 3:
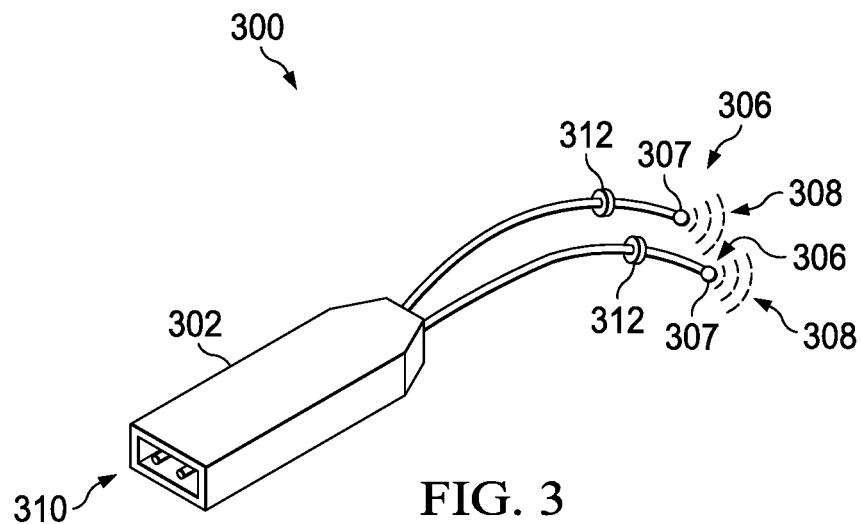
FIG. 3 is an illustration of an exemplary handpiece to treat a base of a tongue according to the present disclosure.

FIG. 3 shows an example of a handpiece 300 which can be utilized to treat the base of the tongue. The handpiece 300 can include handle 302, dual electrodes 306 which can include temperature sensors 307, stops 312, RF power 308, and cord receptacle 310. The handpiece 300 may have any number of electrodes 306, including 1, 2, 3, or more. As with electrodes 206, electrodes 306 may be penetrating or surface electrodes. FIG. 3 shows an exemplary handpiece 300 with two piercing or penetrating electrodes 306. With penetrating electrodes 306, the handpiece 300 can include stops 312 to prevent the penetrating electrodes 306 from penetrating to a further depth. As such, the penetrating electrodes 306 can only penetrate to a desired depth. Similar to FIG. 2, the electrodes 306 are configured to emit RF power 308. The temperature sensors 307 can be integrated with the electrodes 306. In other examples, the temperature sensors 307 can be separate components. The temperature sensors 307 can measure the temperature of the region treated with the RF power 308. As such, if the temperature of the treated region becomes too high, the electrodes 306 may be instructed to emit less RF power 308 and/or stop emitting RF power 308. As such, the handpiece 300 can maintain the temperature of the treated region and avoid burning or destroying tissue. The handpiece 300 can then prevent scarring or extreme discomfort to the patient.

Features discussed for handpieces 200 and 300 are exemplary and can be utilized within any example handpiece as desired.

Figure 4:
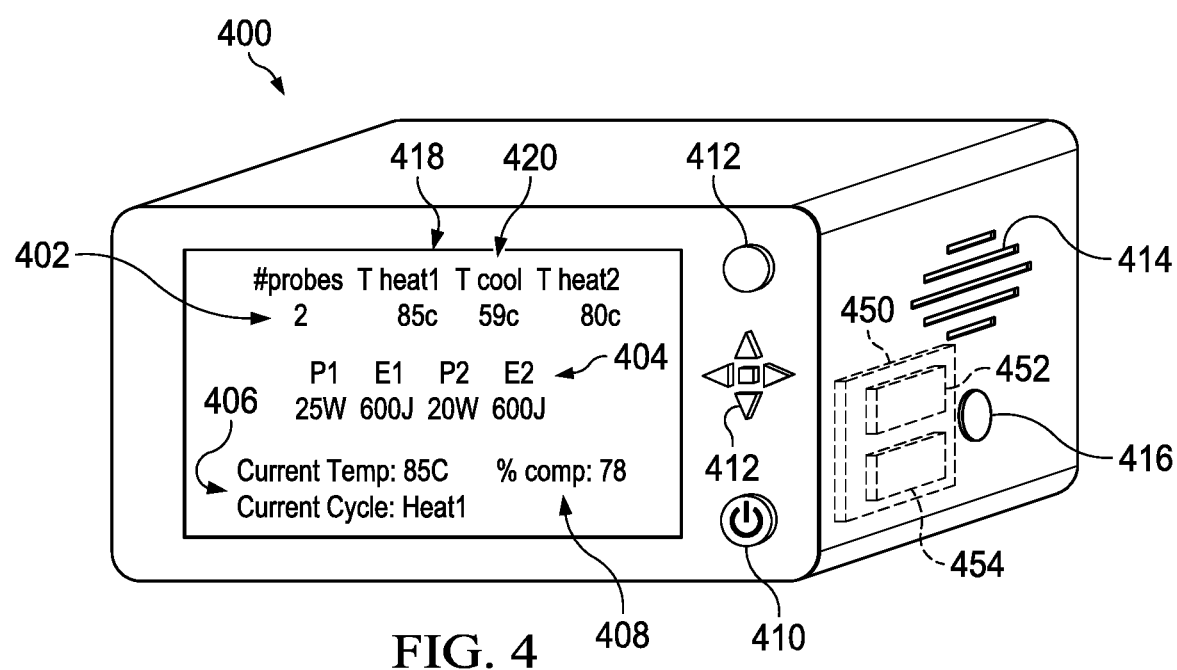
FIG. 4 is an illustration of an exemplary workstation according to the present disclosure.

FIG. 4 shows an example of workstation 400. Workstation 400 can include power switch 410, controls 412, speaker 414, microphone 416, and/or display 418. Controls 412 can be utilized for actions selected from the list including but not limited to programming workstation 400, setting temperatures, time durations, powers, energies, number of heating cycles, etc. It will be understood that display 418 can have any number of factory or user configured screens and can have different screens for different procedures and for different cycles or phases of a given procedure. FIG. 4 shows an example of a screen of display 418, with a screen displaying the number of probes display 402, temperature settings display 420, power and energy settings display 404, current status display 406, and percent complete display 408, described in further detail below. Workstation 400 can include speaker 414 to provide audio status information to the user during the procedure, and optional microphone 416 for receiving verbal instructions from the user during the procedure. Workstation 400 also includes connectors on the back panel (not shown) for connecting peripheral devices. In at least one example, the features of the workstation 400 can be implemented within a handpiece. Workstation 400 can also include a processing system 450 configured to control the handpiece. For example, the workstation 400 may receive data from temperature sensors and adjust the electrodes emitting RF energy accordingly. The processing system 450 can include a processor 452 and a memory 454. The memory 454 can include instructions which are processed by the processor 452 to control the handpiece.

Figure 5:
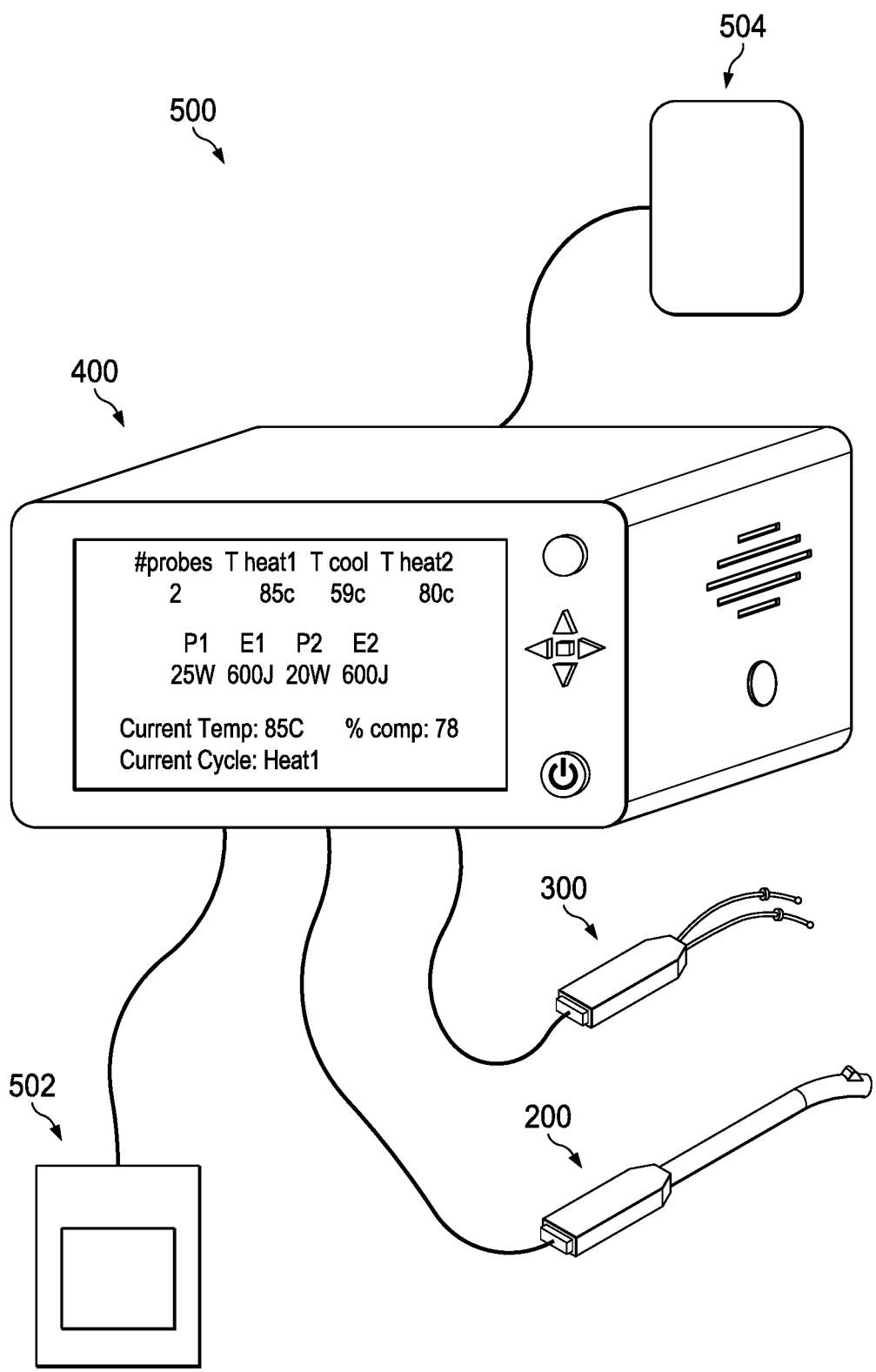
FIG. 5 is an illustration of an exemplary system or kit according to the present disclosure.

FIG. 5 displays an exemplary kit or system 500. In the exemplary system 500 displayed in FIG. 5, system 500 includes workstation 400, foot pedal 502, soft palate handpiece 200, base of tongue handpiece 300, and/or grounding pad 504. Foot pedal 502, soft palate handpiece 200, base of tongue 108 handpiece 300, and grounding pad 504 are coupled to workstation 400 via cables and connectors (not shown), for example on the back of workstation 400.

An exemplary use of system 500 is an improved method to treat sleep apnea via RF ablation of base of tongue 110, RF ablation of soft palate 102, and/or a sequential combination of the two treatments. The method can involve any number of distinct treatments to base of tongue 110, for example from 1 to 10 treatments, from 2 to 8 treatments, or from 4 to 6 treatments. The treatments to base of tongue 110 are separated by an interval of about a day or more, an interval of from about 1 week to about 10 weeks, an interval of from about 2 weeks to about 6 weeks, or an interval of from about 3 to about 5 weeks. The method can involve any number of distinct treatments to soft palate 102, preferably from 1 to 6 treatments, more preferably from 1 to 5 treatments, still more preferably 2 to 5 treatments. The treatments to soft palate 102 are separated by an interval of about a day or more, an interval from about 1 weeks to about 20 weeks, an interval from about 2 weeks to about 15 weeks, an interval from about 4 to about 12 weeks, or an interval from about 7 weeks to about 9 weeks. In at least one example, the treatment or treatments to base of tongue 110 can be completed first, followed by the treatments to soft palate 102. In at least one example, the first soft palate treatment can be performed immediately, for example during the same appointment within a predetermined amount of time such as 30 minutes or an hour, after the last base of tongue treatment. Alternatively, the first soft palate treatment may be delayed from the last base of tongue treatment by an interval of about a day or more, an interval of from about 1 week to about 10 weeks, an interval of from about 2 weeks to about 6 weeks, or an interval of from about 3 to about 5 weeks. For example, the method can include 5 treatments, each separated by about 4 weeks. All five treatments can include a treatment of base of tongue 110. The first, third, and fifth treatments can include a treatment of soft palate 102.

Base of the Tongue Procedure.

The treatment of base of tongue 110 can be conducted with handpiece 300 including handle 302, one or more of electrodes 306 which can be piercing or penetrating electrodes 306 with stops 312 that set the depth of piercing. The electrodes 306 can include the temperature sensor 307 for monitoring the temperature of the treatment area. In at least one example, each electrode 306 includes the temperature sensor 307. In other examples, the temperature sensor 307 can be a separate component. System 500 can include a cable for connecting handpiece 300 to workstation 400 and/or a power source. In at least one example, penetrating electrodes 306 can be bent in a way that facilitates insertion of the one or more electrodes 306 in base of tongue 110. Handpiece handle 302 can be shaped in a way that facilitates holding of handpiece 300 while penetrating electrodes 306 are inserted without obstructing the view of the area of base of tongue 110 being treated. In at least one example, electrodes 306 are bent to an angle that facilitates insertion into the tongue. In at least one example, handpiece 300 has a single electrode 306. Handpiece 300 can have more than two electrodes 306. As illustrated in FIG. 3, handpiece 300 has two electrodes 306. In the description that follows, handpiece 300 includes two electrodes 306. Although two electrodes 306 are used, RF power 308 can be unipolar with a separate grounding pad, rather than bipolar, where the electric field is applied between the two electrodes 306. It is to be understood that if handpiece 300 includes one electrode 306 (and similarly for more than two electrodes 306) that a very similar procedure can be used. For the example of one electrode 306, the RF power and total RF energy delivered would be half that of a system with two electrodes. Time durations, temperatures, impedances, and the like would be essentially the same independent of the numbers of electrodes 306. In the case of one electrode 306, the entire procedure, including injection of tumescence fluid, can be repeated one or more times to compensate for the number of electrodes.

The treatment can be conducted with the use of workstation 400 as shown in FIG. 3. Workstation 400 has functions that can include but are not limited to: reading out the signal from a temperature sensor and converting it to a temperature, measuring the impedance between one or more electrodes 306 and grounding pad 504, supplying RF power 308 to electrodes 306, controlling RF power 308 to ensure that a previously set temperature has not been exceeded, integrating the RF power over time to calculate the total delivered RF energy, turning off RF power 308 when a condition has been met, including but not limited to a time and a total energy delivered, and repetitions and combinations thereof. Workstation 400 can include a front panel with display 418 which displays information related to the procedure and controls 412 which allow for the programming and/or selection of a procedure. Workstation 400 can have connectors on the front and/or the back, to couple components including but not limited to one or more types of handpieces, grounding pad 504, foot pedal 502, and a power cord (not shown). Workstation 400 can be mains powered, but can have any type of power source, including but not limited to battery power. Workstation 400 can include one or more systems for giving notifications to the user during a procedure, including but not limited to front panel display 418, light indicators for example light emitting diodes, and a sound or sounds from speaker 414.

The method includes attaching grounding pad 504 to the subject and attaching grounding pad 504 via a cable to workstation 400. Grounding pad 504 can be attached to the subject's lower back.

The method includes a mechanism for the user to control workstation 400 during the treatment. The mechanism for controlling workstation 400 during the treatment may include controls 412 which may include switches or buttons on the front panel. In at least one example, the mechanism for controlling workstation 400 can function without touching workstation 400 during the treatment, freeing up the hands and attention of the user. Mechanisms for controlling workstation 400 can include but are not limited to voice recognition via microphone 416, and foot pedal 502. In at least one example, the mechanism for controlling workstation 400 can be activated less than 10 times during a single treatment, less than 6 times, or less than 4 times. In an example, the mechanism for controlling workstation 400 is activated only once at the start of the treatment, and the rest of the treatment is pre-programmed.

The treatment can start with a patient pre-operative briefing. The briefing can be oral, and optionally includes an instruction booklet. Preferably the briefing can include the prescription of antibiotics and cortico-steroids by a physician when clinically indicated. Sample antibiotics include but are not limited to 500 mg cephalexin 3 times per day for 7 days. If the patient is allergic to penicillin, doxycycline, 100 mg, twice daily, 7 days may be substituted. Sample corticosteroids include but are not limited to Medrol (4 mg methylprednisolone) Dosepak; dosed as follows: Day 1: Two tablets before breakfast, one after lunch, one after dinner, and two at bedtime. If started late in the day, take all six tablets at once or divide into two or three doses, unless otherwise directed by prescriber. Day 2: One tablet before breakfast, one after lunch, one after dinner, and two at bedtime. Day 3: One tablet before breakfast, one after lunch, one after dinner, and one at bedtime. Day 4: One tablet before breakfast, one after lunch, and one at bedtime. Day 5: One tablet before breakfast and one at bedtime. Day 6: One tablet before breakfast. Alternative, the corticosteroid can be depomedrol (40 mg) & dexamethasone (4 mg) given in a single intramuscular shot immediately after the procedure.

The method includes programming of workstation 400. Programming may involve the setting of individual parameters, including but not limited to power levels, time durations, total energy delivered, minimum temperatures to start a portion of the treatment, and time delays between phases of the treatment. The programming includes the selection of a treatment from a list of treatments. The list of treatments may be created by the care provider, or they may be factory preset. In at least one example, the factory procedures may be updatable, for example from the internet via wifi or similar wireless communication protocol. The care provider has the option of creating new procedures by modifying existing procedures, and also has the option of creating new procedures from scratch.

The method can include sterilization of the mouth, for example by the use of a mouthwash such as Listerine.

During the procedure the tip of tongue 108 is held, for example by the patient, to ensure that tongue 108 does not move, and potentially cause movement or retraction of electrodes 306 during the procedure. In order to facilitate holding of tongue 108, a means to improve grip, preferably gauze, is used.

The surface of tongue 108 can be treated with a topical anesthetic, for example 2 sprays of Hurricaine Topical Anesthetic spray (Benzocaine 200 mg) prior to the injection of a local anesthetic.

The method can include delivery of a local anesthetic, for example 2.5 cc of lidocaine (2%) at the locations of electrode 306 insertion.

In at least one example, the injection can include, in addition to local anesthetic, a tumescence fluid to produce swelling and firmness of the treatment area. The inventor of the present inventive concept has discovered that the use of tumescence fluid significantly improves the efficacy of the treatment, and is at least in part responsible for the improved results over conventional methods. Tumescence fluids may include lidocaine (for example 0.05% or 0.1%), normal saline solution (0.9%), and epinephrine (for example 1:1,000,000). In some examples, the tumescence fluid includes 0.5 cc-10 cc of lidocaine solution, 1 cc-5 cc, or 2 cc-3 cc. The concentration of the lidocaine can be between 0.05% and 5% by weight, between 0.1% and 4%, or between 1% and 3%. The Tumescence fluid can include 0.1 cc-5 cc of sodium bicarbonate, 0.2 cc-1 cc, or 0.3 cc-0.7 cc. The concentration of the sodium bicarbonate can be between 1% and 15% by weight, between 3% and 11%, or between 7% and 10%. In some examples, the Tumescence fluid includes 0.1 cc-10 cc of bacteriostatic normal saline solution (0.9%), 0.5 cc-5 cc, or 1 cc-3 cc. The tumescence solution can include about 5 parts (50%) of 2% lidocaine, about 1 part (10%) sodium bicarbonate 8.4%, and about 4 parts (40%) bacteriostatic normal saline solution (0.9%).

After injection of the tumescence fluid, the method can include waiting a predetermined period of time before inserting electrodes 306. The predetermined time is the minimum time for the local anesthetic to begin to take effect, or before the local anesthetic has completely taken effect. Longer times can result in the distribution of the tumescence fluid away from the treatment site or sites, resulting in reduced efficacy. Wait times can include about 10 seconds to about 3 minutes, about 20 seconds to about 2 minutes, or about 30 seconds to about 1 minute. In at least one example, the target time between delivery of the local anesthetic and start of the procedure is about 45 seconds.

After waiting the predetermined time, electrodes 306 can be inserted in tongue 108, for example with electrodes 306 positioned within the region affected by the injection of the tumescence fluid. The method can include monitoring the insertion to ensure that the caregiver feels two "pops," a "pop" being a portion of the insertion characterized by increased required force and reduced insertion rate, followed by a portion of the insertion at higher rate and lower force. One pop is associated with the exterior of the tongue, the other is associated with a layer within the tongue. The care provider can ensure that the RF emitting portion of electrodes 306 are fully buried beneath the surface of tongue 108 to avoid burning of the surface mucosal tissue. For example, stop 312 can limit further insertion of the electrodes 306 into the tongue 108.

When the insertion of electrodes 306 is complete, the procedure is started, for example essentially immediately. As discussed above, the procedure can be started by any of several different ways. For example, the procedure can be started by depressing foot switch or foot pedal 502.

When the procedure is started, workstation 400 begins the heating phase of the first RF ablation cycle. Workstation 400 turns on the RF power by providing power to the electrodes 306 which emit RF power 308. Workstation 400 also can begin monitoring the temperature at one or more of electrodes 306 by the temperature sensors 307. The RF power during this phase may be between about 1 watt and 100 watts (0.5 watts to 50 watts per electrode 306), between about 3 watts and about 50 watts (1.5 watt to 25 watts per electrode 306), or between about 5 watts and about 30 watts (2.5 watt to 15 watts per electrode 306). The heating phase can last between 10 seconds and 70 seconds, or between 20 seconds and 50 seconds. The procedure has a target temperature that was previously programmed or selected, and during this heating phase, RF power is supplied until the temperature reaches the target temperature. In at least one example, the maximum RF power the instrument is capable of is applied during this phase. In other examples, the maximum power is applied unless the rate of temperature increase exceeds a preset value in which case the RF power is reduced until the rate of temperature increase is below the preset value. The maximum rate of increase at the beginning of the first ablation cycle can be less than about 3° C. per second, less than 2° C. per second, or less than or equal to about 1.5° C. per second. The target temperature for the first ablation cycle can be between about 60° C. and about 110° C., between about 75° C. and 95° C., or between about 80° C. and 90° C. For example, the target temperature is about 85° C. The temperature of the region can be measured by the temperature sensors 307. During the first RF ablation cycle there can be a target total energy delivery. The target total energy delivered can be between about 300 Joules (J) and about 2000 Joules (150 to 1000 Joules per electrode 306), between about 400 J and about 800 J (200 to 400 Joules per electrode 306), or between about 500 J and about 700 J (250 to 350 Joules per electrode 306). For example, the target energy can be about 600 J (300 J per electrode 306). In some cases the target temperature will not be reached before the target energy is delivered. In this case the ablation cycle will consist solely of the heating phase. However, in other cases the target temperature will be reached before the target energy is delivered, resulting in a maintenance phase where workstation 400 determines the RF power required to maintain the temperature at the target temperature. This maintenance RF power can be between about 1 watt and 100 watts (0.5 watts to 50 watts per electrode 306), between about 3 watts and 60 watts (1.5 watts to 30 watts per electrode 306), or between about 4 watts and about 40 watts (2 watts to 20 watts per electrode 306).

After the target energy has been delivered, workstation 400 enters a cooling cycle where RF power is decreased or is not emitted. The duration of the cooling cycle can be between about 2 seconds and about 40 seconds, between about 5 seconds and about 30 seconds, or between about 8 seconds and 22 seconds. The cooling cycle may continue until a cooling target temperature is reached. The temperature of the region can be measured by the temperature sensors 307. The cooling target temperature is between about 30° C. and about 90° C., between about 40° C. and about 80° C., or between about 50° C. and about 70° C. For example, the cooling target temperature is about 59° C. The position of the electrodes 306 can be maintained during the cooling cycle.

Following the cooling cycle, a second RF ablation cycle can be conducted. Electrodes 306 can continue to be positioned in the location where they were inserted during the first RF ablation cycle. The parameters to be selected can include but are not limited to the RF power, target temperature, maximum rate of temperature increase, and total RF energy, and may be the same as or different from those of the first RF ablation cycle. Similar to the first RF ablation cycle, workstation 400 turns on RF power 308 and begins monitoring the temperature at each electrode in the heating phase. The RF power during this phase may be between about 1 watt and 100 watts (0.5 watt to 50 watts per electrode), between about 3 watts and about 50 watts (1.5 watt to 25 watts per electrode), or between about 5 watts and about 30 watts (2.5 watt to 15 watts per electrode). The heating phase can last between 10 seconds and 70 seconds, or between 20 seconds and 50 seconds. The procedure has a target temperature that was previously programmed or selected, and during this heating phase, RF power 308 is supplied until the temperature reaches the target temperature. In at least one example, the maximum RF power the instrument is capable of is applied during this phase. In another example, the maximum power is applied unless the rate of temperature increase exceeds a preset value. The maximum rate of increase at the beginning of the second ablation cycle is less than about 3° C. per second, less than 2° C. per second, or less than or equal to about 1.5° C. per second. The target temperature for the second ablation cycle can be between about 60° C. and about 110° C., between about 75° C. and 95° C., or between about 80° C. and 90° C. For example, the target temperature is about 85° C. During the second RF ablation cycle there is a target total energy delivery. The target total energy delivered can be between about 300 Joules and about 2000 Joules (150 to 1000 Joules per electrode 306), between about 400 J and about 800 J (200 to 400 Joules per electrode 306), between about 500 J and about 700 J (250 to 350 Joules per electrode 306). For example, the target energy is about 600 J (300 J per electrode 306). In some cases, the target temperature may not be reached before the target energy is delivered. In this case the ablation cycle will consist solely of the heating phase. However, in other cases the target temperature will be reached before the target energy is delivered, resulting in a maintenance phase wherein workstation 400 determines the RF power required to maintain the temperature at the target temperature. This maintenance RF power can be between about 1 watt and 100 watts (0.5 watts to 50 watts per electrode), between about 3 watts and 60 watts (1.5 watts to 30 watts per electrode), or between about 4 watts and about 40 watts (2 watts to 20 watts per electrode).

FIG. 4 shows an exemplary screen of display 418, wherein 2 electrodes 306 are used, there are two RF ablation cycles separated by one cooling cycle, the first RF ablation cycle has a target temperature of 85° C., the second RF ablation cycle has a target temperature of 80° C., the two RF ablation cycles are separated by a cooling cycle with a target cool down temperature of 59° C. The first RF ablation cycle has a maximum RF power of 25 watts and a target RF energy of 600 J. The second RF ablation cycle has a maximum RF energy of 20 watts, and like the first RF ablation cycle, the second RF ablation cycle has a target RF energy of 600 J. The illustrated system is currently in the first RF ablation cycle (denoted by "Heat1"), and the heating phase has been completed as the temperature has reached 85° C., so the system is in the maintenance phase. The first RF ablation cycle is 78% complete.

The above cooling and RF ablation cycles may be conducted any number of additional times, with the same or different heating, ablation and cooling parameters. For example, the procedure can include two RF ablation cycles separated by a single cooling cycle.

After the desired number of RF ablation and heating cycles, electrodes 306 are removed from tongue 108 and handpiece 300 is removed from the patient's mouth 118. The patient is instructed to hold tongue 108 against the roof of their mouth 118 for a predetermined amount of time. The handpiece and cable may be durable and reusable after a procedure. In at least one example, the handpiece and/or the cable are disposed of after the procedure.

Electrodes 306 may be optionally replaced with unused electrodes 306, and the procedure repeated. In at least one example, the procedure is only conducted with one pair of electrode 306 locations per visit.

Soft Palate Procedure.

The method can include combining the base of the tongue procedure discussed above with a soft palate procedure. In at least one example, on some visits (see discussion above) the treatment of base of tongue 110 can be followed by treatment of soft palate 102. In other examples, the soft palate procedure is done on a separate, dedicated clinic visit. In general, the course of treatment for a given patient may involve both dedicated soft palate procedure visits, dedicated base of the tongue procedure visits, and visits wherein both the base of the tongue and the soft palate procedure are carried out.

The soft palate portion of method can include programming of workstation 400. As with the base of tongue portion of the method, the programming may involve the setting of individual parameters, including but not limited to: power levels, time durations, total energy delivered, minimum temperatures to start a portion of the treatment, and time delays between phases of the treatment. In at least one example, the programming can include the selection of a treatment from a list of treatments. The list of treatments may be created by the care provider, or they may be factory preset, or the list of treatments may comprise both types of treatments. In at least one example, the factory procedures may be updatable, for example from the internet, for example via wifi or similar wireless communication protocol. The care provider can have the option of creating new procedures by modifying existing procedures, and also has the option of creating new procedures from scratch.

In at least one example, the workstation 400 is the same as the one used in base of tongue portion of the method and a single grounding pad is used. In other examples, workstation 400 may be a different workstation from the one used for the treatment of base of tongue 110. In the example where both procedures are performed during one visit, and where workstation 400 is different from that used for the base of tongue treatment, grounding pad 504 cord will have to be transferred to the second workstation, or if grounding pad 504 or its cord is not compatible with the second workstation, a new grounding pad will have to be applied.

Each treatment of soft palate 102 can be conducted with handpiece 200 including grip or handle 202, one or more of electrodes 206, one or more temperature sensors 207 on each electrode 206 for monitoring the temperature of the treatment area, and a cable for connecting handpiece 200 to workstation 400. In at least one example, electrodes 206 are surface electrodes. Electrodes 206 may also be piercing electrodes, bent in a way that facilitates insertion of the one or more electrodes 206 into soft palate 102. The handle 202 can be shaped in a way that facilitates holding of the handpiece while electrodes 206 are inserted into or pressed against soft palate 102 while not obstructing the view of the area of soft palate 102 being treated. As illustrated in FIG. 2, handpiece 200 has the single electrode 306. It is to be understood that if handpiece 200 has more than one electrode 206 that a very similar procedure can be used. For an example including two electrodes 206, the RF power and total RF energy delivered would be twice that of a system with one electrode 206. Time durations, temperatures, impedances, and the like would be the same independent of the numbers of electrodes 206. In the description that follows, it will be assumed that handpiece 200 has a single surface electrode 206. The disclosure is intended to cover any number of electrodes 206, and the use of piercing electrodes, with modifications to the method as described above and in the base of the tongue procedure section.

Prior to injection of a topical anesthetic, the patient can be treated with an anti-emetic to reduce gag reflex. One exemplary anti-emetic is a topically applied anti-nausea ointment. A location for application can be the wrist. One exemplary anti-nausea ointment is 0.1 ml of Phenergan/promethazine (25 mg/0.1 ml).

Soft palate 102 can be treated with a topical anesthetic, for example 1 spray to the palatal area of Hurricaine Topical Anesthetic spray (Benzocaine 200 mg) prior to the injection of a local anesthetic. The method can include delivery of a local anesthetic, for example about 1.0 cc of lidocaine (2%), injected at either side of soft palate 102.

After waiting a predetermined time, electrode 206 can be pressed onto the surface of soft palate 102 and the procedure is started, for example essentially immediately. If penetrating electrodes are utilized, the method can be adjusted as in the discussion above regarding the base of tongue treatment. As discussed above, the procedure can be started by any of several different ways. For example, the procedure is started by depressing foot pedal 502.

When the procedure is started, workstation 400 begins an RF tissue tightening cycle. Workstation 400 provides power to the electrodes 206 to emit RF energy 208 and begins monitoring the temperature of soft palate 102 in the location of electrode 206. The RF power during this phase may be between about 1 watt and 100 watts, between about 3 watts and about 50 watts, or between about 5 watts and about 30 watts. The procedure has a target temperature, and electrode 206 is held in position until the temperature of the treated region reaches or exceeds the target temperature. The temperature sensors 207 can measure the temperature of the area treated with the RF energy 208. The temperature sensors 207 can be integrated with the electrodes 306. In other examples, the temperature sensors 207 can be separate components. In at least one example, the target temperature for the is between about 37° C. and about 60° C., between about 38° C. and 50° C., or between about 39° C. and about 45° C. For example, the target temperature can be about 40° C. The care giver or user can be notified of the temperature of the treated region as it is difficult to look at display 418 on workstation 400 while conducting the procedure. In at least one example, the notification may be provided by a second person, such as a nurse. In other examples, the user is notified by another means, for example a tone or a recorded message via speaker 414. Electrode 206 is held in a given location for between about 1 second and about 10 seconds, between about 2 seconds and about 7 seconds, or between about 3 seconds and about 5 seconds. When the target temperature is achieved, electrode 206 can be removed and pressed into a different location of soft palate 102, and above steps are repeated. Over the course of the soft palate procedure, substantially the entire area of soft palate 102 is treated. For example, between about 10 and about 40 locations are treated, or between about 15 and about 30 locations are treated. The procedure can be run for a maximum duration when workstation 400 shuts off RF energy 208. The maximum duration can be between about 30 seconds and about 200 seconds, between about 60 seconds and about 120 seconds, or between about 80 seconds and about 100 seconds. For example, the maximum duration is about 90 seconds. The care giver or user may have an option to stop the timer and the delivery of RF power if, for example, he or she need an extended time for activity between electrode placements. This can be accomplished through any number of ways, such as foot pedal 502 and/or voice command via microphone 416.

After the time limit is reached, handpiece 200 is removed from the patient's mouth. Handpiece 200 and its cable may be durable and reusable after a procedure. In other examples, the handpiece 200 and cable are both disposed of after the procedure. Grounding pad 504 can also be removed and disposed.

In at least one example, workstation 400 or workstations 400 are used to carry out the above procedures.

In some examples, any of the handpieces 200 and 300 are used to carry out the above procedures, without the need of full workstations 400. The handpieces 200 may have the full capability to perform the functions of the workstation 400.

In other examples, a kit can include components including but not limited to one or more instruction leaflets, one or more workstations, one or more handpieces, one or more grounding pads, one or more power cords, one or more injection needles and syringes, and topical and local anesthetics, tumescence fluids, anti-emetics, antibiotics, anti-inflammatories, and gauzes.

EXAMPLES

Example 1

A clinical study using the disclosed method and procedure was conducted in 14 males aged 39 to 77. The study design was a baseline sleep study, followed by 5 courses of the base of the tongue procedure as described above, followed by a second sleep study. Subsequently, the subjects were given 3 courses of the soft palate procedure as described above, followed by a third sleep study. During the sleep studies, AHI, REM AHI (AHI during REM sleep) time and percent time below 90% oxygen saturation, minimum oxygen saturation, and time and percent time snoring were measured. Snoring was defined as significant if above 45 dB.

During the first sleep study, 6 of the subjects were found to have moderate obstructive sleep apnea (15≤AHI<30) and 7 of the subjects were found to have severe sleep apnea (AHI≥30). The average AHI in the moderate to severe population was 41.2. One subject had only very mild sleep apnea, with an AHI of 7.9. For the subjects with moderate to severe OSA, the average baseline REM AHI was 36.6, the average number of minutes with oxygen saturation below 90% was 47.1 minutes, the average percent time with oxygen saturation below 90% was 11.0%, and average minimum oxygen saturation was 78.0%. On average, the subjects snored for 91 minutes, or 22.6% of the time they were asleep.

Following the above-discussed 5 courses of treatment to the base of the tongue and 3 courses of treatment to the soft palate, there was a very significant decrease in the moderate to severe population in AHI of 11.9. The p value for this decrease was 0.004 despite the relatively small sample size. The larger change was due to the soft palate procedure, with an improvement in AHI of 7.9. During REM sleep, the REM AHI decreased by 9.5, with a p value of 0.008. Again, the largest improvement was in the soft palate procedure, with a reduction in REM AHI of 11.1. The percent time below 90% oxygen saturation decreased by 19.1 minutes (p<0.05), and the percent time below 90% oxygen saturation decreased from 11.0 to 4.4%. The minimum oxygen saturation over the course of the study increased by 1.5 percentage points to 80.2%. There was a marked, >50% decrease in the total amount of sleep time spent snoring, from a baseline average of 95.8 minutes down to 38.6 minutes (p<0.005). On a percentage basis, the decrease in time was from 22.6% to 10.6% (p<0.001).

Example 2

66 patients with mild, moderate, or severe obstructive sleep apnea were recruited into a clinical study. Each patient first underwent a baseline sleep study, wherein a number of parameters were assessed. Key parameters included API and oxygen saturation.

Subjects then came into the clinic one or more times wherein the base of the tongue procedure described above was conducted. The procedure was comprised of two RF ablation cycles applied to the base of tongue, separated by one cooling cycle. A two-electrode handpiece similar to that shown in FIG. 3 was used. The parameters used for the first and second RF ablation cycle were the same. The target temperature during the RF ablation cycle was 85° C. The target energy was 600 Joules. The cooling target temperature was 59° C. The procedure was repeated up to 5 times, based on their response and the severity of their condition.

The average baseline AHI for all patients was 36.7±20.6 (standard deviation). Post treatment, the average AHI for all patients dropped very significantly, to 11.4±11.3. The average decrease in AHI was 25.4±18.2. Using a paired one-sided t test, the p value for this decrease was $2.69*10^{-17}$.

At baseline, the average percent of the time while asleep that oxygen saturation was less than 90% was 11.2±12.4% (data only available for 54 of the subjects). After the procedure, the percent time below 90% dropped significantly to 7.0±4.7%, with a p value of 0.0014.

At baseline, the average minimum percent oxygen saturation was 76.2±8.5% (data only available for 57 of the subjects). After the procedure the minimum percent oxygen saturation increased significantly, to 83±5.8%. The p value was 0.000018

Comparison to Conventional Procedure

The conventional procedure has been studied in a way that is directly comparable to the data discussed above (Steward, D: *Effectiveness of Multilevel (Tongue and Palate) Radiofrequency Tissue Ablation for Patients with Obstructive Sleep Apnea Syndrome* Laryngoscope 114: December 2004). Table 1 presents the comparison:

TABLE 1

|  | Prior Art Method | | | | Current Invention | | | |
| --- | --- | --- | --- | --- | --- | --- | --- | --- |
|  | n | Ave | SEM | P Value | n | Ave | SEM | P Value |
| Baseline AHI: | 22 | 31.0 | 3.8 |  | 66 | 36.7 | 2.6 |  |
| Change in AHI: | 22 | −12.2 | 3.5 | 0.001 | 66 | −25.4 | 2.3 | <.0001 |
| Baseline minimum O2 saturation, % | 22 | 84.9 | 2.1 |  | 57 | 76.2 | 1.1 |  |
| Change in minimum O2 saturation, % | 22 | 0.1 | 1.6 | 0.96 | 57 | 6.2 | 1.2 | <.0001 |

|  |  | % |  |  | % |
| --- | --- | --- | --- | --- | --- |
| AHI Reduction of >50%, to AHI <20, % | 22 | 59.0 |  | 66 | 76.9 |
| AHI Reduction of >50%, to AHI <15, % | 22 | 45.0 |  | 66 | 70.8 |
| AHI Reduction of >50%, to AHI <10, % | 22 | 36.0 |  | 66 | 60.0 |

As can be seen in Table 1, in spite of the fact that only the base of the tongue procedure as disclosed herein was used, versus the combination of base of the tongue and soft palate in the conventional procedure, the procedure as disclosed herein achieved significantly more reduction in AHI, −25.4 vs. −12.2 for the conventional method. The conventional method did not achieve any significant increase in minimum O2 saturation, (P=0.96) while the procedure as disclosed herein achieved a very significant increase of 6.2 percentage points as described above.

Steward also presented his data in terms of the percent of patients that achieved at least a 50% reduction in AHI, and achieved a final AHI of <20, <15, and <10. The two datasets are compared in FIG. 6.

As can be seen in FIG. 6 and Table 1, the procedure as disclosed herein significantly outperformed the conventional procedure, with 77%, 71%, and 60% achieving a 50% or greater reduction in AHI and a final AHI of less than 20, 15, and 20, respectively. Each of the three results using the back of the tongue procedure as disclosed herein achieved an AHI outside of the 95% confidence interval of the Steward results.

Numerous examples are provided herein to enhance understanding of the present disclosure. A specific set of statements are provided as follows.

Statement 1: A system is disclosed to treat sleep apnea, the system comprising: a handpiece including: at least one penetrating electrode configured to penetrate tissue; and one or more temperature sensors; a processor coupled with the one or more temperature sensors and the at least one penetrating electrode; and a memory configured to store instructions executable by the processor, the instructions, when executed, are operable to: emit, by the at least one penetrating electrode, RF energy from the electrodes to heat a region of a base of a tongue until a target energy is delivered to the region; and measure, by the one or more temperature sensors, the temperature of the region.

Statement 2: A system is disclosed according to Statement 1, wherein when treating the base of the tongue, the instructions when executed, are further operable to: conduct a first radiofrequency (RF) ablation cycle by emitting the RF energy from the at least one penetrating electrode positioned at the region of the base of the tongue until a first target energy is delivered to the region; pause the emitting of the RF energy from the at least one penetrating electrode for a predetermined period of cooling time; measure, by the one or more temperature sensors, the temperature of the region until a target cooling temperature is reached; and after the target cooling temperature is reached, conduct a second RF ablation cycle by heating the region of the tongue by emitting RF energy from the at least one penetrating electrode until a second target energy is delivered to the region.

Statement 3: A system is disclosed according to Statements 1 or 2, further including a microphone coupled with the processor, the microphone configured to receive verbal instructions.

Statement 4: A system is disclosed according to Statement 3, wherein the verbal instructions include activating and de-activating the at least one penetrating electrode.

Statement 5: A system is disclosed according to any of preceding Statements 1-4, further including a foot pedal coupled with the processor, wherein activation of the foot pedal activates and de-activates the at least one penetrating electrode.

Statement 6: A system is disclosed to treat sleep apnea, the system comprising: a handpiece including: at least one surface electrode; and one or more temperature sensors; a processor coupled with the one or more temperature sensors and the at least one surface electrode; and a memory configured to store instructions executable by the processor, the instructions, when executed, are operable to: emit, by the at least one surface electrode, RF energy to heat a region of a soft palate of a subject until a target temperature of the region is reached; and measure, by the one or more temperature sensors, the temperature of the region.

Statement 7: A system is disclosed according to Statement 6, wherein when treating the soft palate, the instructions when executed, are further operable to: press the at least one surface electrode against the region of the soft palate; after the target temperature is reached, emit RF energy, by the at least one surface electrode, to the region to maintain the target temperature of the region for a predetermined period of time; and de-activate the at least one surface electrode after the predetermined period of time is reached.

Statement 8: A system is disclosed according to Statements 6 or 7, further including: a microphone coupled with the processor, the microphone configured to receive verbal instructions.

Statement 9: A system is disclosed according to Statement 8, wherein the verbal instructions include activating and de-activating the at least one surface electrode.

Statement 10: A system is disclosed according to any of preceding Statements 6-9, further including: a foot pedal coupled with the processor, wherein activation of the foot pedal activates and de-activates the at least one surface electrode.

Statement 11: A method is disclosed to treat sleep apnea, the method comprising: conducting a first radiofrequency (RF) ablation cycle by emitting RF energy from at least one electrode positioned at a region at a base of a tongue of a subject until a first target energy is delivered to the region; pausing the emitting of the RF energy from the at least one electrode for a predetermined period of cooling time; measuring, by one or more temperature sensors, the temperature of the region until a target cooling temperature is reached; and after the target cooling temperature is reached, conducting a second RF ablation cycle by heating the region of the tongue by emitting RF energy from the at least one electrode until a second target energy is delivered to the region.

Statement 12: A method is disclosed according to Statement 11, wherein the first RF ablation cycle is the same as the second RF ablation cycle.

Statement 13: A method is disclosed according to Statements 11 or 12, wherein the first RF ablation cycle is different than the second RF ablation cycle.

Statement 14: A method is disclosed according to any of preceding Statements 11-13, wherein the first target energy is between about 500 J and about 700 J.

Statement 15: A method is disclosed according to any of preceding Statements 11-14, wherein the first target energy is about 600 J.

Statement 16: A method is disclosed according to any of preceding Statements 11-15, wherein the second target energy is between about 500 J and about 700 J.

Statement 17: A method is disclosed according to any of preceding Statements 11-16, wherein the second target energy is about 600 J.

Statement 18: A method is disclosed according to any of preceding Statements 11-17, wherein the target cooling temperature is between about 50° C. and about 70° C.

Statement 19: A method is disclosed according to any of preceding Statements 11-18, wherein the target cooling temperature is about 59° C.

Statement 20: A method is disclosed according to any of preceding Statements 11-19, wherein, during the first RF ablation cycle, the region is a first temperature less than or equal to a first target heating temperature; wherein, during the second RF ablation cycle, the region is a second temperature less than or equal to a second target heating temperature.

Statement 21: A method is disclosed according to Statement 20, wherein the first target heating temperature is between about 80° C. and 90° C.

Statement 22: A method is disclosed according to Statements 20 or 21, wherein the first target heating temperature is about 85° C.

Statement 23: A method is disclosed according to any of preceding Statements 20-22, wherein the second target heating temperature is between about 80° C. and 90° C.

Statement 24: A method is disclosed according to any of preceding Statements 20-23, wherein the second target heating temperature is about 85° C.

Statement 25: A method is disclosed according to any of preceding Statements 11-24, wherein the at least one electrode is a penetrating electrode, and the at least one electrode penetrates a surface of the region of the tongue.

Statement 26: A method is disclosed according to any of preceding Statements 11-25, further comprising: attaching to the subject a grounding pad coupled to the at least one electrode.

Statement 27: A method is disclosed according to any of preceding Statements 11-26, further comprising: injecting a tumescence fluid in the region of the tongue; and positioning the at least one electrode at the region at the base of the tongue of the subject.

Statement 28: A method is disclosed according to Statement 27, wherein the tumescence fluid includes local anesthetic, saline solution, and sodium bicarbonate.

Statement 29: A method is disclosed according to Statements 27 or 28, wherein the tumescence fluid is injected prior to the positioning of the at least one electrode.

Statement 30: A method is disclosed to treat sleep apnea, the method comprising: pressing at least one surface electrode against a region of a soft palate of a subject; emitting radiofrequency (RF) energy from the at least one surface electrode to the region; measuring, by one or more temperature sensors, the region until a target temperature is reached at the region; and when the target temperature is reached, holding the at least one surface electrode at the region for a predetermined period of time.

Statement 31: A method is disclosed according to Statement 30, wherein the target temperature is between about 39° C. and about 45° C.

Statement 32: A method is disclosed according to Statements 30 or 31, wherein the target temperature is about 40° C.

Statement 33: A method is disclosed according to any of preceding Statements 30-32, wherein the predetermined period of time is between about 2 seconds and about 7 seconds.

Statement 34: A method is disclosed according to any of preceding Statements 30-33, wherein the predetermined period of time is between about 3 seconds and about 5 seconds.

Statement 35, A method is disclosed according to any of preceding Statements 30-34, further comprising: moving the at least one surface electrode to another region of the soft palate; pressing at least one surface electrode against the another region; emitting radiofrequency (RF) energy from the at least one surface electrode to the another region until another target temperature is reached at the region; when the another target temperature is reached, holding the at least one surface electrode at the region for another predetermined period of time.

Statement 36: A method is disclosed according to any of preceding Statements 30-35, further comprising: attaching to the subject a grounding pad coupled to the at least one electrode.

Statement 37: A method is disclosed to treat sleep apnea, the method comprising: conducting a first radiofrequency (RF) ablation cycle by emitting RF energy from at least one penetrating electrode inserted into a tongue region at a base of a tongue of a subject until a first target energy is delivered to the tongue region; pausing the emission of the RF energy from the at least one electrode for a predetermined period of cooling time; measuring, by one or more temperature sensors, the temperature of the region until a target cooling temperature is reached; after the target cooling temperature is reached, conducting a second RF ablation cycle by heating the tongue region by emitting RF energy from the at least one electrode until a second target energy is delivered to the tongue region; pressing at least one surface electrode against a soft palate region of the soft palate of the subject; emitting radiofrequency (RF) energy from the at least one surface electrode to the soft palate region until a target temperature is reached at the soft palate region; and when the target temperature is reached, holding the at least one surface electrode at the soft palate region for a predetermined period of time.

Statement 38: A method is disclosed according to Statement 37, wherein the first RF ablation cycle is the same as the second RF ablation cycle.

Statement 39: A method is disclosed according to Statements 37 or 38, wherein the first RF ablation cycle is different than the second RF ablation cycle.

Statement 40: A method is disclosed according to any of preceding Statements 37-39, wherein the first target energy is between about 500 J and about 700 J.

Statement 41: A method is disclosed according to any of preceding Statements 37-40, wherein the first target energy is about 600 J.

Statement 42: A method is disclosed according to any of preceding Statements 37-41, wherein the second target energy is between about 500 J and about 700 J.

Statement 43: A method is disclosed according to any of preceding Statements 37-42, wherein the second target energy is about 600 J.

Statement 44: A method is disclosed according to any of preceding Statements 37-43, wherein the target cooling temperature is between about 50° C. and about 70° C.

Statement 45: A method is disclosed according to any of preceding Statements 37-44, wherein the target cooling temperature is about 59° C.

Statement 46: A method is disclosed according to any of preceding Statements 37-45, wherein, during the first RF ablation cycle, the region is a temperature less than or equal to a first target heating temperature; wherein, during the second RF ablation cycle, the region is a temperature less than or equal to a second target heating temperature.

Statement 47: A method is disclosed according to Statement 46, wherein the first target heating temperature is between about 80° C. and 90° C.

Statement 48: A method is disclosed according to Statements 46 or 47, wherein the first target heating temperature is about 85° C.

Statement 49: A method is disclosed according to any of preceding Statements 46-48, wherein the second target heating temperature is between about 80° C. and 90° C.

Statement 50: A method is disclosed according to any of preceding Statements 46-49, wherein the second target heating temperature is about 85° C.

Statement 51: A method is disclosed according to any of preceding Statements 37-50, further comprising: attaching to the subject a grounding pad coupled to the at least one electrode.

Statement 52: A method is disclosed according to any of preceding Statements 37-51, further comprising: injecting a tumescence fluid in the tongue region; inserting the at least one penetrating electrode at the tongue region.

Statement 53: A method is disclosed according to Statement 52, wherein the tumescence fluid includes local anesthetic, saline solution, and sodium bicarbonate.

Statement 54: A method is disclosed according to Statements 52 or 53, wherein the tumescence fluid is injected prior to the positioning of the at least one penetrating electrode.

Statement 55: A method is disclosed according to any of preceding Statements 37-54, wherein the target temperature is between about 39° C. and about 45° C.

Statement 56: A method is disclosed according to any of preceding Statements 37-55, wherein the target temperature is about 40° C.

Statement 57: A method is disclosed according to any of preceding Statements 37-56, wherein the predetermined period of time is between about 2 seconds and about 7 seconds.

Statement 58: A method is disclosed according to any of preceding Statements 37-57, wherein the predetermined period of time is between about 3 seconds and about 5 seconds.

Statement 59: A method is disclosed according to any of preceding Statements 37-58, further comprising: moving the at least one surface electrode to another soft palate region of the soft palate; pressing at least one surface electrode against the another soft palate region; emitting radiofrequency (RF) energy from the at least one electrode to the another soft palate region until another target temperature is reached at the soft palate region; when the another target temperature is reached, holding the at least one surface electrode at the soft palate region for another predetermined period of time.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

What is claimed is:

1. A system to treat sleep apnea, the system comprising:
a handpiece including:
at least one penetrating electrode configured to penetrate tissue at a base of a tongue, and
one or more temperature sensors;
a processor coupled with the one or more temperature sensors and the at least one penetrating electrode; and
a memory configured to store instructions executable by the processor, the instructions, when executed, are operable to:
conduct a first radiofrequency (RF) ablation cycle, while the at least one penetrating electrode is penetrating into a location in the base of the tongue, by emitting RF energy from the at least one penetrating electrode to a region of the base of the tongue until a first target energy is delivered to the region;
pause the emitting of the RF energy from the at least one penetrating electrode for a predetermined period of cooling time;
measure, by the one or more temperature sensors while the emitting of the RF energy is paused, the temperature of the region until a target cooling temperature is reached; and
after the target cooling temperature is reached, conduct a second RF ablation cycle, with the at least one penetrating electrode remaining in the location in the base of the tongue, by heating the region of the tongue by emitting RF energy from the at least one penetrating electrode until a second target energy is delivered to the region.

2. The system of claim 1, further including:
a microphone coupled with the processor, the microphone configured to receive verbal instructions.

3. The system of claim 2, wherein the verbal instructions include activating and de-activating the at least one penetrating electrode.

4. The system of claim 1, further including:
a foot pedal coupled with the processor, wherein activation of the foot pedal activates and de-activates the at least one penetrating electrode.

5. A method to treat sleep apnea, the method comprising:
conducting a first radiofrequency (RF) ablation cycle, while at least one penetrating electrode is penetrating into a location in a base of a tongue of a subject, by emitting RF energy from the at least one electrode positioned at a region at the base of the tongue until a first target energy is delivered to the region;
pausing the emitting of the RF energy from the at least one electrode for a predetermined period of cooling time;
measuring, by one or more temperature sensors, the temperature of the region until a target cooling temperature is reached; and
after the target cooling temperature is reached, conducting a second RF ablation cycle, with the at least one penetrating electrode remaining in the location in the base of the tongue, by heating the region of the tongue by emitting RF energy from the at least one electrode until a second target energy is delivered to the region.

6. The method of claim 5, wherein the first target energy is between about 500 J and about 700 J.

7. The method of claim 5, wherein the second target energy is between about 500 J and about 700 J.

8. The method of claim 5, wherein the target cooling temperature is between about 50° C. and about 70° C.

9. The method of claim 5,
wherein,
during the first RF ablation cycle, the region is a first temperature less than or equal to a first target heating temperature, and
during the second RF ablation cycle, the region is a second temperature less than or equal to a second target heating temperature.

10. The method of claim 5, wherein the at least one electrode is a penetrating electrode, and the at least one electrode penetrates a surface of the region of the tongue.

11. The method of claim 5, further comprising:
injecting a tumescence fluid in the region of the tongue; and
positioning the at least one electrode at the region at the base of the tongue of the subject.

* * * * *